US010508264B2

(12) United States Patent
Ohta et al.

(10) Patent No.: US 10,508,264 B2
(45) Date of Patent: *Dec. 17, 2019

(54) CELL CULTURE METHOD USING BONE MARROW-LIKE STRUCTURE, AND POROUS POLYIMIDE FILM FOR HEALING BONE INJURY SITE

(71) Applicants: UBE INDUSTRIES, LTD., Ube-shi, Yamaguchi (JP); KURUME UNIVERSITY, Kurume-shi, Fukuoka (JP)

(72) Inventors: Keisuke Ohta, Kurume (JP); Shingo Hirashima, Kurume (JP); Masahiko Hagihara, Ube (JP); Motohisa Shimizu, Ube (JP)

(73) Assignees: UBE INDUSTRIES, LTD., Yamaguchi (JP); KURUME UNIVERSITY, Fukuoka (JP)

(*) Notice: Subject to any disclaimer, the term of this patent is extended or adjusted under 35 U.S.C. 154(b) by 0 days.

This patent is subject to a terminal disclaimer.

(21) Appl. No.: 15/958,995

(22) Filed: Apr. 20, 2018

(65) Prior Publication Data

US 2018/0237750 A1    Aug. 23, 2018

Related U.S. Application Data

(62) Division of application No. 15/546,047, filed as application No. PCT/JP2016/052215 on Jan. 26, 2016.

(30) Foreign Application Priority Data

Jan. 26, 2015  (JP) ................................ 2015-012696
Jan. 26, 2015  (JP) ................................ 2015-012743

(51) Int. Cl.
*C12N 5/077* (2010.01)
*C08J 9/00* (2006.01)
(Continued)

(52) U.S. Cl.
CPC ............ *C12N 5/0669* (2013.01); *A61L 27/18* (2013.01); *A61L 27/3608* (2013.01); *A61L 27/56* (2013.01);
(Continued)

(58) Field of Classification Search
CPC .................................................. A61L 2430/02
See application file for complete search history.

(56) References Cited

U.S. PATENT DOCUMENTS 5,275,602 A     1/1994  Shimizu et al.
6,911,201 B1    6/2005  Merchav et al.
(Continued)

FOREIGN PATENT DOCUMENTS

EP    3 026 108 A1    6/2016
EP    3 252 145 A1    12/2017
(Continued)

OTHER PUBLICATIONS

International Search Report dated Apr. 5, 2016 corresponding to International Patent Application No. PCT/JP/2016/052215, filed on Jan. 26, 2016; 3 pages.
(Continued)

*Primary Examiner* — Michael B. Pallay
(74) *Attorney, Agent, or Firm* — Mintz Levin Cohn Ferris Glovsky and Popeo PC

(57) ABSTRACT

The present invention relates to a method for culturing bone marrow cells, in which bone marrow cells are applied to a porous polyimide film and cultured. Moreover, the present invention relates to a porous polyimide film for healing a bone injury site.

9 Claims, 9 Drawing Sheets

(51) Int. Cl.
  *C12N 1/00* (2006.01)
  *A61L 27/18* (2006.01)
  *A61L 27/36* (2006.01)
  *A61L 27/56* (2006.01)
  *C12N 5/0789* (2010.01)

(52) U.S. Cl.
  CPC .............. *C08J 9/00* (2013.01); *C12N 1/00* (2013.01); *C12N 5/0647* (2013.01); *A61L 2430/02* (2013.01); *C12N 2501/14* (2013.01); *C12N 2533/30* (2013.01)

(56) References Cited

U.S. PATENT DOCUMENTS

| | | | |
|---|---|---|---|
| 2004/0241145 | A1 | 12/2004 | Hata et al. |
| 2009/0010896 | A1 | 1/2009 | Centeno et al. |
| 2011/0082565 | A1 | 4/2011 | Tzezana et al. |
| 2011/0318556 | A1 | 12/2011 | Ohya et al. |
| 2012/0316646 | A1 | 12/2012 | Gretzer et al. |
| 2014/0017284 | A1 | 1/2014 | Yang et al. |
| 2016/0002599 | A1* | 1/2016 | Eto .............. C12N 5/0644 435/373 |
| 2016/0168560 | A1* | 6/2016 | Hagihara .......... C12M 25/02 435/180 |
| 2018/0148693 | A1 | 5/2018 | Ohta et al. |

FOREIGN PATENT DOCUMENTS

| | | | |
|---|---|---|---|
| JP | 63-196286 | A | 8/1988 |
| JP | 63-198975 | A | 8/1988 |
| JP | 63-198978 | A | 8/1988 |
| JP | 3029266 | B | 4/2000 |
| JP | 2002-535981 | A | 10/2002 |
| JP | 3421741 | B | 6/2003 |
| JP | 2006-230683 | A | 9/2006 |
| JP | 4412537 | B | 2/2010 |
| JP | 2010-532370 | A | 10/2010 |
| JP | 2011-219585 | A | 11/2011 |
| JP | 2011-219586 | A | 11/2011 |
| JP | 4950269 | B | 6/2012 |
| WO | 00/46349 | A1 | 8/2000 |
| WO | 2002/076285 | A2 | 10/2002 |
| WO | 2007/015546 | A1 | 2/2007 |
| WO | 2010/038873 | A1 | 4/2010 |
| WO | 2015/012415 | A1 | 1/2015 |
| WO | WO-2015012415 | A1 * | 1/2015 ............ C12M 25/02 |
| WO | 2015/163043 | A1 | 10/2015 |

OTHER PUBLICATIONS

Julien, Sylvie et al., "Implantation of ultrathin, biofunctionalized polyimide membranes into the subretinal space of rats," *Bomaterials* (Mar. 8, 2011 online); 32:3890-3898.

Kim, Sang-Bok et al., "Use of a poly(ether imide) coating to improve corrosion resistance and biocompatibility of magnesium (Mg) implant for orthopedic applications," *Journal of Biomedical Materials Research A* (Jun. 2013; published online Nov. 27, 2012); 101A(6):1708-1715.

Lyons, Frank G. et al., "The healing of bony defects by cell-free collagen-based scaffolds compared to stem cell-seeded tissue engineered constructs," *Biomaterials* (Sep. 22, 2010); 31:9232-9243.

Maenosono, Hirotaka et al., "Cultivation of OP9 Cells onto Organic Flexible Sheets with Transferred Micropatterns," *IEICE Technical Report* (Apr. 2013) 113(18):37-42 (see, English Abstract).

Mikalayeva, Valeryia et al., "Application of polyimide films for cell scaffold in tissue engineering," *Acta Physiologica* (Nov. 2015); 215(705):137; Abstract #P10-7.

Raic, Annamarja et al., "Biomimetic macroporous PEG hydrogels as 3D scaffolds for the multiplication of human hematopoietic stem and progenitor cells," *Biomaterials* (2014; avail online Oct. 28, 2013); 35:929-940.

Tao, Chun-Te et al., "Polyetherimide membrane formation by the cononsolvent system and its biocompatibility of MG63 cell line," *Journal of Membrane Science* (2006; accepted Jun. 10, 2005); 269:66-74.

Wu, Shuilin et al., "Biomimetic porous scaffolds for bone tissue engineering," *Materials Science and Engineering R*, (May 5, 2014); 80:1-36.

European Search Report corresponding to EP 16743374.7 dated Jul. 6, 2018, 8 pages.

Maenosono, Hirotaka et al., "A Transparent Polyimide Film as a Biological Cell Culture Sheet with Microstructures," *Journal of Biomaterials and Nanobiotechnology* (2014; accepted Dec. 28, 2013); 5:17-23.

Ouyang, H. W. et al., "Characterization of anterior cruciate ligament cells and bone marrow stromal cells on various biodegradable polymeric films," *Materials Science and Engineering* (May 1, 2002); 29(1-2):63-69.

Rossi, Filippo et al., "Polymeric scaffolds as stem cell carriers in bone repair," *J Tissue Eng Regen Med* (2013; accepted Aug. 30, 2013); 27 pages.

* cited by examiner

Porous polyimide film-fixed image after 7 days of additional culturing
(blue:nuclei, green:GFP)

B-surface large hole structure and CD45-positive cells
(blue:nuclei, green:GFP, red:CD45)

CELL CULTURE METHOD USING BONE MARROW-LIKE STRUCTURE, AND POROUS POLYIMIDE FILM FOR HEALING BONE INJURY SITE

TECHNICAL FIELD

The present invention relates to cell culturing using a bone marrow-like structure having a three-dimensional culture support. More specifically, it relates to cell culturing using a bone marrow-like structure with a porous polyimide film. The invention further relates to a flexible porous sheet for healing of bone injury sites. More specifically, it relates to a porous polyimide film for healing of bone injury sites.

BACKGROUND ART

Cell Culturing

Cells generally exist as three-dimensional aggregates in the body, but in classical plate culturing, cells are cultured in a monolayer fashion with the cells attached to a vessel. Numerous reports have indicated significant differences in cell properties with different culturing environments.

Bone marrow-related cells have a strong tendency to be affected by the scaffold of the culturing environment in which they grow, and many cases have been reported in which cell culturing is promoted using three-dimensional culture supports. PTL 1 discloses a bioreactor that employs a method utilizing a nonwoven fiber matrix that forms a three-dimensional fiber network, to increase and maintain undifferentiated hematopoietic stem cells or hematopoietic precursor cells isolated from a body, when they are outside of the body. Use of a nonwoven fabric is also disclosed in NPL 1 and elsewhere. The stem cell properties of hematopoietic stem cells are known to be easily lost, but NPL 2 teaches that by synthesizing a porous hydrogel and culturing hematopoietic stem cells on it, it is possible to maintain the stem cell properties of the hematopoietic stem cells in a manner specific to the cell source. A more direct case is reported in PTL 2, describing efficient adhesion of bone marrow stem cells by seeding the cells on the surface of a support composed of a calcium phosphate-based compound. In addition, PTL 3 reports that Oshima et al. of the University of Tsukuba seeded and cultured cells recovered from mouse bone marrow on a collagen-treated three-dimensional scaffold formed of polyvinyl formal and transplanted them into mouse dorsal regions, by which they were able to function as artificial bone marrow. However, no sufficiently practical methodology has yet been established.

Moreover, while spatial structure has been shown by previous inventions to be in a strict proportion to function and efficiency, demonstrating the importance of a three-dimensional scaffold structure, this has been approached from the point of view of the general concept of "spatial structure", or from the viewpoint of bone marrow-like composition or size control of the porous structure, and not from the viewpoint of morphology or anatomy, in terms of similarity of morphological structure. It is desirable to establish a method of culturing bone marrow cells designed from a novel viewpoint that is directed toward establishing a more efficient and highly practical methodology.

Bone Injury and Healing

With a view toward patient QOL, healing of bone injuries, including fractures and bone loss, has traditionally employed techniques using a variety of tools and means, involving methods of anchoring plates or screws in the affected areas. In recent years, bone disease treatment materials and implements with various structural, functional and biocompatible features have been created and utilized in medicine (NPL 3 and PTL 4). In regenerative medicine as well, different methods have been employed in attempts to promote healing of bone injuries including fractures and bone loss, and for example, there have been reports of methods of supplementing affected areas with compound materials obtained by culturing cells such as mesenchymal stem cells in biomaterials such as collagen or apatite, or bioabsorbable materials (PTLs 5 and 6). The therapeutic efficacy of stem cells and the extent to which they contribute has been a matter of dispute (NPL 4).

Such methods are mainly characterized in that materials composed of biological substances, or cell-containing biological substances, or combinations of cells and autolytic substances, are used in the body to supplement wounds or deficient sites, but in some cases these methods are not suitable, for sites with extensive damage or loss or for complex shapes, and in other cases the methods are very time consuming.

In the field of dentistry, certain operations involve leaving a space in the wound area while forming a film on the surface (NPL 5). Such techniques are designed to avoid rapid epithelial formation in the wound area, but are not widely applicable for bone regeneration.

There is demand for a convenient and effective method of treating bone injury that is suitable for a variety of wound surfaces including sites with extensive loss and sites with complex shapes.

Porous Polyimide Film

The term "polyimide" is a general term for polymers including imide bonds in the repeating unit. An "aromatic polyimide" is a polymer in which aromatic compounds are directly linked by imide bonds. An aromatic polyimide has an aromatic-aromatic conjugated structure via an imide bond, and therefore has a strong rigid molecular structure, and since the imide bonds provide powerful intermolecular force, it has very high levels of thermal, mechanical and chemical properties.

Porous polyimide films have been utilized in the prior art for filters and low permittivity films, and especially for battery-related purposes, such as fuel cell electrolyte membranes and the like. PTLs 7 to 9 describe porous polyimide films with numerous macro-voids, having excellent permeability for gases and the like, high porosity, excellent smoothness on both surfaces, relatively high strength and, despite high porosity, also excellent resistance against compression stress in the film thickness direction. All of these are porous polyimide films formed via amic acid.

CITATION LIST

Patent Literature

[PTL 1] WO2000/046349
[PTL 2] Japanese Patent No. 4393908
[PTL 3] Japanese Patent No. 3421741
[PTL 4] Japanese Patent No. 3029266
[PTL 5] Japanese Patent No. 4412537
[PTL 6] Japanese Patent No. 4950269
[PTL 7] WO2010/038873
[PTL 8] Japanese Unexamined Patent Publication No. 2011-219585
[PTL 9] Japanese Unexamined Patent Publication No. 2011-219586

NON-PATENT LITERATURE

[NPL 1] Funakoshi News, October 1st issue in 2012
[NPL 2] A. Raic et al./Biomaterials 35 (2014) 929-940

[NPL 3] F. G. Lyons et al./Biomaterials 31 (2010) 9232-9243
[NPL 4] S. Wu et al./Materials Science and Engineering R 80 (2014) 1-36
[NPL 5] GC Corporation, GC Membrane Manual

DISCLOSURE OF THE INVENTION

Problems to be Solved by the Invention

It is an object of the present invention to provide a more efficient and highly practical method of culturing bone marrow cells. It is another object of the invention to provide convenient and effective means for treating bone injury, that is applicable for many different wound surfaces.

Means for Solving the Problems

The present inventors have found that the spatial structure of a porous polyimide film, which is an organic thin-film, morphologically approximates the structure of bone marrow. It was further found that culturing bone marrow cells using the porous polyimide film allows proliferation of CD45-positive cells. Surprisingly, it was also found that when the porous polyimide film is used for culturing of bone marrow cells, a cell mass is produced having differentiating characteristics similar to bone marrow, while following the spatial structure of the porous polyimide film. It was yet further found that using a differentiation-inducing accelerator can cause differentiation of the cultured cells to erythroid progenitor cells within the porous polyimide film.

The present inventors still further found that a porous polyimide film with a spatial structure morphologically approximating bone marrow structure can be used for healing of bone injury sites.

The present invention preferably includes, but is not limited to, the following modes.

[Mode 1]
A method of culturing bone marrow cells that includes applying bone marrow cells to a porous polyimide film and culturing them.

[Mode 2]
The method according to mode 1, wherein the bone marrow cells are marrow stromal cells.

[Mode 3]
The method according to mode 1, wherein the bone marrow cells are bone marrow-derived blood cells.

[Mode 4]
The method according to any one of modes 1 to 3, wherein the bone marrow cells are cells harvested from mammalian bone marrow.

[Mode 5]
The method according to any one of modes 1 to 3, wherein the bone marrow cells are primary cultured cells from cells harvested from mammalian bone marrow.

[Mode 6]
The method according to any one of modes 1 to 5, further including differentiation of bone marrow cells to hematocytes by culturing.

[Mode 7]
The method according to any one of modes 1 to 6, further including applying bone marrow cells to a porous polyimide film and then adding a differentiation-inducing accelerating substance and culturing, to accelerate differentiation from the bone marrow cells to hematocytes in a manner specific to the spatial structure of the porous polyimide film.

[Mode 8]
The method of preparing hematocytes, including recovering hematocytes obtained using a method according to mode 6 or 7.

[Mode 9]
The method according to any one of modes 6 to 8, wherein the hematocytes are erythroid progenitor cells or erythrocytes.

[Mode 10]
The method of culturing bone marrow cells including:
(1) a step of applying a first cell group to a porous polyimide film and culturing it, and
(2) a step of applying a second cell group to the porous polyimide film after the culturing in step (1), and culturing it,
wherein the second cell group consists of bone marrow cells.

[Mode 11]
The method according to mode 10, wherein the first cell group is selected from the group consisting of animal cells, insect cells, plant cells, yeast cells and bacteria.

[Mode 12]
The method according to mode 11, wherein the first cell group consists of bone marrow cells derived from a mammal.

[Mode 13]
The method according to any one of modes 10 to 12, further including differentiation of bone marrow cells to hematocytes by the culturing in step (2).

[Mode 14]
The method according to any one of modes 10 to 13, further including applying the second cell group in step (2) to a porous polyimide film and then adding a differentiation-inducing accelerating substance and culturing, to accelerate differentiation from the bone marrow cells, as the second cell group, to hematocytes in a manner specific to the spatial structure of the porous polyimide film.

[Mode 15]
A method of preparing hematocytes, including recovering hematocytes obtained using a method according to mode 13 or 14.

[Mode 16]
The method according to any one of modes 13 to 15, wherein the hematocytes are erythroid progenitor cells or erythrocytes.

[Mode 17]
The method according to any one of modes 1 to 16, wherein the porous polyimide film is a porous polyimide film including a polyimide obtained from a tetracarboxylic dianhydride and a diamine.

[Mode 18]
The method according to mode 17, wherein the porous polyimide film is a colored porous polyimide film obtained by forming a polyamic acid solution composition including a polyamic acid solution obtained from a tetracarboxylic dianhydride and a diamine, and a coloring precursor, and then heat treating it at 250° C. or higher.

[Mode 19]
The method according to mode 17 or 18, wherein the porous polyimide film is a porous polyimide film with a multilayer structure, having two different surface layers and a macro-void layer.

[Mode 20]
The method according to any one of modes 1 to 19, using two or more porous polyimide films layered either above and below or left and right in the cell culture medium.

[Mode 21]

The method according to any one of modes 1 to 20, wherein the porous polyimide film is:
  i) folded,
  ii) wound into a roll,
  iii) connected as sheets or fragments by a filamentous structure, or
  iv) bound into a rope, and used by suspension or anchoring in the cell culture medium in the cell culturing vessel.

[Mode 22]

A kit for use in the method according to any one of modes 1 to 21, including a porous polyimide film.

[Mode 23]

Use of a porous polyimide film for the method according to any one of modes 1 to 21.

[Mode 24]

A porous polyimide film for healing of a bone injury site.

[Mode 25]

The porous polyimide film according to mode 24, wherein the bone injury is a fracture.

[Mode 26]

The porous polyimide film according to mode 24, wherein the bone injury is bone loss.

[Mode 27]

The porous polyimide film according to any one of modes 24 to 26, which is to be used for transplantation into the body in contact with an affected area of bone injury.

[Mode 28]

The porous polyimide film according to any one of modes 24 to 27, which is a porous polyimide film including a polyimide obtained from a tetracarboxylic dianhydride and a diamine.

[Mode 29]

The porous polyimide film according to mode 28, which is a colored porous polyimide film obtained by forming a polyamic acid solution composition including a polyamic acid solution obtained from a tetracarboxylic dianhydride and a diamine, and a coloring precursor, and then heat treating it at 250° C. or higher.

[Mode 30]

The porous polyimide film according to mode 28 or 29, which is a porous polyimide film with a multilayer structure, having two different surface layers and a macro-void layer.

[Mode 31]

The porous polyimide film according to mode 30, which is to be used for transplantation into the body in such a manner that of the two different surface layers, the surface with the smaller mean pore size is in contact with the affected area of bone injury.

[Mode 32]

The porous polyimide film according to any one of modes 24 to 31, wherein the film thickness of the porous polyimide film is no greater than 100 micrometers.

[Mode 33]

The porous polyimide film according to any one of modes 24 to 32, wherein the surface of the porous polyimide film is treated by a step of modifying its physical properties.

[Mode 34]

The porous polyimide film according to mode 33, wherein the step of modifying the physical properties of the surface of the porous polyimide film is selected from the group consisting of a step of alkali treatment of the surface of the porous polyimide film, a step of calcium treatment, a step of covering with a biocompatible material, and a combination of any of these steps.

[Mode 35]

The method according to mode 34, wherein the biocompatible material is selected from the group consisting of collagen, fibronectin, laminin, polylysine, polylactide, polyglycolide, polycaprolactone, polyhydroxybutyrate, polylactide-co-caprolactone, polycarbonate, biodegradable polyurethane, polyether ester, polyesteramide, hydroxyapatite, collagen/β-TCP complex, and combinations of the foregoing.

[Mode 36]

The porous polyimide film according to any one of modes 24 to 35 on which cells have been supported beforehand.

[Mode 37]

The porous polyimide film according to mode 36, wherein the cells are cells selected from the group consisting of mammal-derived pluripotent stem cells, tissue stem cells, somatic cells, and combinations of the foregoing.

[Mode 38]

The porous polyimide film according to mode 37, wherein the cells include mammal-derived bone marrow cells.

[Mode 39]

A kit for healing of a bone injury site, including a porous polyimide film according to any one of modes 24 to 38.

[Mode 40]

Use of a porous polyimide film according to any one of modes 24 to 38 for healing of a bone injury site.

[Mode 41]

A method for producing a porous polyimide film for healing of a bone injury site, the method including supporting bone marrow cells on a porous polyimide film.

[Mode 42]

The method according to mode 41, wherein the bone marrow cells are harvested from a target of healing of a bone injury site.

[Mode 43]

A method of healing a bone injury site, including applying a porous polyimide film according to any one of modes 24 to 38 to a bone injury site.

Effect of the Invention

The present invention utilizes the spatial structure of a porous polyimide film that is morphologically similar to bone marrow structure, to allow efficient culturing of bone marrow cells. According to the invention, it is possible to obtain cells with differentiating characteristics similar to bone marrow, that also follow the characteristic spatial structure of a porous polyimide film. No material with such a function has been reported to date. According to the invention, it is also possible to cause differentiation of cultured cells to erythroid progenitor cells in a porous polyimide film. The invention can be applied for providing blood components with reduced infection risk and immunological rejection risk.

Moreover, by using a porous polyimide film which is a flexible porous sheet, the invention can be applied to a variety of wound surfaces including sites with extensive damage or loss or sites with complex shapes, to allow convenient and efficient healing of bone injuries. The porous polyimide film to be used for the invention is a thin-film surrounded by surfaces with a large open area ratio having two different structures: a mesh structure surface, referred to as the A-surface, and a large hole structure surface, referred to as the B-surface, and having a polyhedral void structure on the interior, the film exhibiting high heat resistance and flexibility, and also excellent shaping freedom. In addition, the porous polyimide film to be used for the invention has a feature whereby it can hold and grow cells inside its characteristic spatial structure. By supporting cells suited for a given purpose on the porous polyimide film and applying them to a bone injury site, it is possible to accelerate healing of the bone injury site.

MODES FOR CARRYING OUT THE INVENTION

Regarding a Porous Polyimide Film

Figure 1:
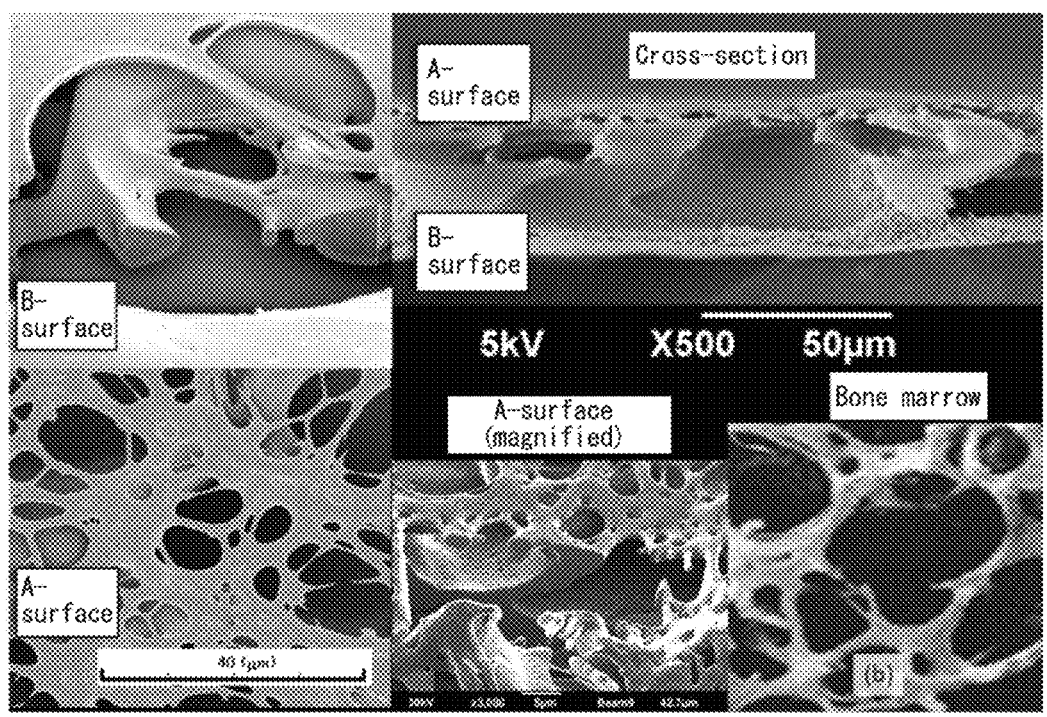
FIG. 1 is a set of scanning electron micrographs of a porous polyimide film having a bone marrow-like structure. A scanning electron micrograph shows a cross-section, and the A-surface (mesh structure surface) and B-surface (large hole structure surface) of the porous polyimide film. For comparison, a scanning electron micrograph of bone marrow published in NPL 1 (Funakoshi News, Oct. 1, 2012 Issue) is also shown (panel (b)).

The present invention relates to I. a method of culturing bone marrow cells, II. a method of culturing bone marrow cells by applying bone marrow cells to a porous polyimide film in two stages, and culturing them, III. a kit to be used in the method of culturing bone marrow cells, IV. use of a porous polyimide film for the method of culturing bone marrow cells, V. a porous polyimide film for healing of a bone injury site, VI. a kit for healing of a bone injury site, VII. use of a porous polyimide film for healing of a bone injury, VIII. a method for producing a porous polyimide film for healing of a bone injury site, and IX. a method of healing a bone injury site. All of these aspects of the invention have in common use of a porous polyimide film.

Polyimide is a general term for polymers containing imide bonds in the repeating unit, and usually it refers to an aromatic polyimide in which aromatic compounds are directly linked by imide bonds. An aromatic polyimide has an aromatic-aromatic conjugated structure via an imide bond, and therefore has a strong rigid molecular structure, and since imide bonds have powerful intermolecular force, it has very high levels of thermal, mechanical and chemical properties.

The porous polyimide film used for the invention is preferably a porous polyimide film including (as the main component) a polyimide obtained from a tetracarboxylic dianhydride and a diamine, and more preferably it is a porous polyimide film comprising a polyimide obtained from a tetracarboxylic dianhydride and a diamine. The phrase "including as the main component" means that it essentially contains no components other than the polyimide obtained from a tetracarboxylic dianhydride and a diamine, as constituent components of the porous polyimide film, or that it may contain them but they are additional components that do not affect the properties of the polyimide obtained from the tetracarboxylic dianhydride and diamine.

The porous polyimide film used for the invention also includes colored porous polyimide films obtained by forming a polyamic acid solution composition containing a polyamic acid solution obtained from a tetracarboxylic acid component and a diamine component, and a coloring precursor, and then heat treating it at 250° C. or higher.

Polyamic Acid

A polyamic acid is obtained by polymerization of a tetracarboxylic acid component and a diamine component. A polyamic acid is a polyimide precursor that can be cyclized to a polyimide by thermal imidization or chemical imidization.

The polyamic acid used may be any one that does not have an effect on the invention, even if a portion of the amic acid is imidized. Specifically, the polyamic acid may be partially thermally imidized or chemically imidized.

When the polyamic acid is to be thermally imidized, there may be added to the polyamic acid solution, if necessary, an imidization catalyst, an organic phosphorus-containing compound, or fine particles such as inorganic fine particles or organic fine particles. Also, when the polyamic acid is to be chemically imidized, there may be added to the polyamic acid solution, if necessary, a chemical imidization agent, a dehydrating agent, or fine particles such as inorganic fine particles or organic fine particles. Even if such components are added to the polyamic acid solution, they are preferably added under conditions that do not cause precipitation of the coloring precursor.

Coloring Precursor

A coloring precursor to be used for the invention is a precursor that generates a colored substance by partial or total carbonization under heat treatment at 250° C. or higher.

Coloring precursors to be used for the invention are preferably uniformly dissolved or dispersed in a polyamic acid solution or polyimide solution and subjected to thermal decomposition by heat treatment at 250° C. or higher, preferably 260° C. or higher, even more preferably 280° C. or higher and more preferably 300° C. or higher, and preferably heat treatment in the presence of oxygen such as air, at 250° C., preferably 260° C. or higher, even more preferably 280° C. or higher and more preferably 300° C. or higher, for carbonization to produce a colored substance, more preferably producing a black colored substance, with carbon-based coloring precursors being most preferred.

The coloring precursor, when being heated, first appears as a carbonized compound, but compositionally it contains other elements in addition to carbon, and also includes layered structures, aromatic crosslinked structures and tetrahedron carbon-containing disordered structures.

Carbon-based coloring precursors are not particularly restricted, and for example, they include tar or pitch such as petroleum tar, petroleum pitch, coal tar and coal pitch, coke, polymers obtained from acrylonitrile-containing monomers, ferrocene compounds (ferrocene and ferrocene derivatives), and the like. Of these, polymers obtained from acrylonitrile-containing monomers and/or ferrocene compounds are preferred, with polyacrylnitrile being preferred as a polymer obtained from an acrylonitrile-containing monomer.

The tetracarboxylic dianhydride used may be any tetracarboxylic dianhydride, selected as appropriate according to the properties desired. Specific examples of tetracarboxylic dianhydrides include biphenyltetracarboxylic dianhydrides such as pyromellitic dianhydride, 3,3',4,4'-biphenyltetracarboxylic dianhydride (s-BPDA) and 2,3,3',4'-biphenyltetracarboxylic dianhydride (a-BPDA), oxydiphthalic dianhydride, diphenylsulfone-3,4,3',4'-tetracarboxylic dianhydride, bis(3,4-dicarboxyphenyl)sulfide dianhydride, 2,2-bis(3,4-dicarboxyphenyl)-1,1,1,3,3,3-hexafluoropropane dianhydride, 2,3,3',4'-benzophenonetetracarboxylic dianhydride, 3,3',4,4'-benzophenonetetracarboxylic dianhydride, bis(3,4-dicarboxyphenyl)methane dianhydride, 2,2-bis(3,4-dicarboxyphenyl)propane dianhydride, p-phenylenebis(trimellitic acid monoester acid anhydride), p-biphenylenebis(trimellitic acid monoester acid anhydride), m-terphenyl-3,4,3',4'-tetracarboxylic dianhydride, p-terphenyl-3,4,3',4'-tetracarboxylic dianhydride, 1,3-bis(3,4-dicarboxyphenoxy)benzene dianhydride, 1,4-bis(3,4-dicarboxyphenoxy)benzene dianhydride, 1,4-bis(3,4-dicarboxyphenoxy)biphenyl dianhydride, 2,2-bis[(3,4-dicarboxyphenoxy)phenyl]propane dianhydride, 2,3,6,7-naphthalenetetracarboxylic dianhydride, 1,4,5,8-naphthalenetetracarboxylic dianhydride, 4,4'-(2,2-hexafluoroisopropylidene)diphthalic dianhydride, and the like. Also preferably used is an aromatic tetracarboxylic acid such as 2,3,3',4'-diphenylsulfonetetracarboxylic acid. These may be used alone or in appropriate combinations of two or more.

Particularly preferred among these are at least one type of aromatic tetracarboxylic dianhydride selected from the group consisting of biphenyltetracarboxylic dianhydride and pyromellitic dianhydride. As a biphenyltetracarboxylic dianhydride there may be suitably used 3,3',4,4'-biphenyltetracarboxylic dianhydride.

Any desired diamine may be used as a diamine. Specific examples of diamines include the following.

1) Benzenediamines with one benzene nucleus, such as 1,4-diaminobenzene(paraphenylenediamine), 1,3-diaminobenzene, 2,4-diaminotoluene and 2,6-diaminotoluene;

2) diamines with two benzene nuclei, including diaminodiphenyl ethers such as 4,4'-diaminodiphenyl ether and 3,4'-diaminodiphenyl ether, and 4,4'-diaminodiphenylmethane, 3,3'-dimethyl-4,4'-diaminobiphenyl, 2,2'-dimethyl-4,4'-diaminobiphenyl, 2,2'-bis(trifluoromethyl)-4,4'-diaminobiphenyl, 3,3'-dimethyl-4,4'-diaminodiphenylmethane, 3,3'-dicarboxy-4,4'-diaminodiphenylmethane, 3,3',5,5'-tetramethyl-4,4'-diaminodiphenylmethane, bis(4-aminophenyl)sulfide, 4,4'-diaminobenzanilide, 3,3'-dichlorobenzidine, 3,3'-dimethylbenzidine, 2,2'-dimethylbenzidine, 3,3'-dimethoxybenzidine, 2,2'-dimethoxybenzidine, 3,3'-diaminodiphenyl ether, 3,4'-diaminodiphenyl ether, 4,4'-diaminodiphenyl ether, 3,3'-diaminodiphenyl sulfide, 3,4'-diaminodiphenyl sulfide, 4,4'-diaminodiphenyl sulfide, 3,3'-diaminodiphenylsulfone, 3,4'-diaminodiphenylsulfone, 4,4'-diaminodiphenylsulfone, 3,3'-diaminobenzophenone, 3,3'-diamino-4,4'-dichlorobenzophenone, 3,3'-diamino-4,4'-dimethoxybenzophenone, 3,3'-diaminodiphenylmethane, 3,4'-diaminodiphenylmethane, 4,4'-diaminodiphenylmethane, 2,2-bis(3-aminophenyl)propane, 2,2-bis(4-aminophenyl)propane, 2,2-bis(3-aminophenyl)-1,1,1,3,3,3-hexafluoropropane, 2,2-bis(4-aminophenyl)-1,1,1,3,3,3-hexafluoropropane, 3,3'-diaminodiphenyl sulfoxide, 3,4'-diaminodiphenyl sulfoxide and 4,4'-diaminodiphenyl sulfoxide;

3) diamines with three benzene nuclei, including 1,3-bis(3-aminophenyl)benzene, 1,3-bis(4-aminophenyl)benzene, 1,4-bis(3-aminophenyl)benzene, 1,4-bis(4-aminophenyl)benzene, 1,3-bis(4-aminophenoxy)benzene, 1,4-bis(3-aminophenoxy)benzene, 1,4-bis(4-aminophenoxy)benzene, 1,3-bis(3-aminophenoxy)-4-trifluoromethylbenzene, 3,3'-diamino-4-(4-phenyl)phenoxybenzophenone, 3,3'-diamino-4,4'-di(4-phenylphenoxy)benzophenone, 1,3-bis(3-aminophenyl sulfide)benzene, 1,3-bis(4-aminophenyl sulfide)benzene, 1,4-bis(4-aminophenyl sulfide)benzene, 1,3-bis(3-aminophenylsulfone)benzene, 1,3-bis(4-aminophenylsulfone)benzene, 1,4-bis(4-aminophenylsulfone)benzene, 1,3-bis[2-(4-aminophenyl)isopropyl]benzene, 1,4-bis[2-(3-aminophenyl)isopropyl]benzene and 1,4-bis[2-(4-aminophenyl)isopropyl]benzene;

4) diamines with four benzene nuclei, including 3,3'-bis(3-aminophenoxy)biphenyl, 3,3'-bis(4-aminophenoxy)biphenyl, 4,4'-bis(3-aminophenoxy)biphenyl, 4,4'-bis(4-aminophenoxy)biphenyl, bis[3-(3-aminophenoxy)phenyl]ether, bis[3-(4-aminophenoxy)phenyl]ether, bis[4-(3-aminophenoxy)phenyl]ether, bis[4-(4-aminophenoxy)phenyl]ether, bis[3-(3-aminophenoxy)phenyl]ketone, bis[3-(4-aminophenoxy)phenyl]ketone, bis[4-(3-aminophenoxy)phenyl]ketone, bis[4-(4-aminophenoxy)phenyl]ketone, bis[3-(3-aminophenoxy)phenyl] sulfide, bis[3-(4-aminophenoxy)phenyl] sulfide, bis[4-(3-aminophenoxy)phenyl] sulfide, bis[4-(4-aminophenoxy)phenyl] sulfide, bis[3-(3-aminophenoxy)phenyl]sulfone, bis[3-(4-aminophenoxy)phenyl]sulfone, bis[4-(3-aminophenoxy)phenyl]sulfone, bis[4-(4-aminophenoxy)phenyl]sulfone, bis[3-(3-aminophenoxy)phenyl]methane, bis[3-(4-aminophenoxy)phenyl]methane, bis[4-(3-aminophenoxy)phenyl]methane, bis[4-(4-aminophenoxy)phenyl]methane, 2,2-bis[3-(3-aminophenoxy)phenyl]propane, 2,2-bis[3-(4-aminophenoxy)phenyl]propane, 2,2-bis[4-(3-aminophenoxy)phenyl]propane, 2,2-bis[4-(4-aminophenoxy)phenyl]propane, 2,2-bis[3-(3-aminophenoxy)phenyl]-1,1,1,3,3,3-hexafluoropropane, 2,2-bis[3-(4-aminophenoxy)phenyl]-1,1,1,3,3,3-hexafluoropropane, 2,2-bis[4-(3-aminophenoxy)phenyl]-1,1,1,3,3,3-hexafluoropropane and 2,2-bis[4-(4-aminophenoxy)phenyl]-1,1,1,3,3,3-hexafluoropropane.

These may be used alone or in mixtures of two or more. The diamine used may be appropriately selected according to the properties desired.

Preferred among these are aromatic diamine compounds, with 3,3'-diaminodiphenyl ether, 3,4'-diaminodiphenyl ether, 4,4'-diaminodiphenyl ether, paraphenylenediamine, 1,3-bis(3-aminophenyl)benzene, 1,3-bis(4-aminophenyl)benzene, 1,4-bis(3-aminophenyl)benzene, 1,4-bis(4-aminophenyl)benzene, 1,3-bis(4-aminophenoxy)benzene and 1,4-bis(3-aminophenoxy)benzene being preferred for use. Particularly preferred is at least one type of diamine selected from the group consisting of benzenediamines, diaminodiphenyl ethers and bis(aminophenoxy)phenyl.

From the viewpoint of heat resistance and dimensional stability under high temperature, the porous polyimide film to be used for the invention is preferably formed from a polyimide obtained by combination of a tetracarboxylic dianhydride and a diamine, having a glass transition temperature of 240° C. or higher, or without a distinct transition point at 300° C. or higher.

From the viewpoint of heat resistance and dimensional stability under high temperature, the porous polyimide film is preferably a porous polyimide film comprising one of the following aromatic polyimides.

(i) An aromatic polyimide comprising at least one tetracarboxylic acid unit selected from the group consisting of biphenyltetracarboxylic acid units and pyromellitic acid units, and an aromatic diamine unit, (ii) an aromatic polyimide comprising a tetracarboxylic acid unit and at least one type of aromatic diamine unit selected from the group consisting of benzenediamine units, diaminodiphenyl ether units and bis(aminophenoxy)phenyl units, and/or, (iii) an aromatic polyimide comprising at least one type of tetracarboxylic acid unit selected from the group consisting of biphenyltetracarboxylic acid units and pyromellitic acid units, and at least one type of aromatic diamine unit selected from the group consisting of benzenediamine units, diaminodiphenyl ether units and bis(aminophenoxy)phenyl units.

While not restrictive, the porous polyimide film for use in the invention may be a porous polyimide film with a multilayer structure, having at least two surface layers (A-surface and B-surface), and a macro-void layer sandwiched between the two surface layers. Preferably, the porous polyimide film is a porous polyimide film wherein the macro-void layer has a partition bonded to the surface layers (A-surface and B-surface) and a plurality of macro-voids with mean pore sizes of 10 to 500 μm in the planar direction of the film, surrounded by the partition and the surface layers (A-surface and B-surface), wherein the macro-void layer partition and the surface layers (A-surface and B-surface) each have thicknesses of 0.01 to 20 μm, with a plurality of pores with mean pore sizes of 0.01 to 100 μm, the pores being optionally communicating with each other, and also having a partial or total multilayer structure in communication with the macro-voids, where the total film thickness is 5 to 500 μm and the porosity is 40% or greater and less than 95%.

The total film thickness of the porous polyimide film used for the invention is not limited, but may be 25 to 75 μm according to one mode. Differences in the film thickness may be observed as differences in cell growth rate, cell morphology, cell saturation within the plate, and the like.

According to the invention, when the porous polyimide film used has two different surface layers (A-surface and B-surface), and a macro-void layer sandwiched between the two surface layers, the mean pore size of the holes in the A-surface may differ from the mean pore size of the holes in the B-surface. Preferably, the mean pore size of the holes in the A-surface is smaller than the mean pore size of the holes in the B-surface. More preferably, the mean pore size of the holes in the A-surface is smaller than the mean pore size of the holes in the B-surface, with the mean pore size of the holes in the A-surface being 0.01 to 50 μm, 0.01 μm to 40 μm, 0.01 μm to 30 μm, 0.01 μm to 20 μm or 0.01 μm to 15 μm, and the mean pore size of the holes in the B-surface being 20 μm to 100 μm, 30 μm to 100 μm, 40 μm to 100 μm, 50 μm to 100 μm or 60 μm to 100 μm. Most preferably, the A-surface of the porous polyimide film is a mesh structure having small holes with a mean pore size of no greater than 15 μm, such as 0.01 μm to 15 μm, and the B-surface is a large-hole structure with a mean pore size of 20 μm or greater, such as 20 μm to 100 μm.

The total film thickness of the porous polyimide film used for the invention can be measured using a contact thickness gauge.

The mean pore size of the surface of the porous polyimide film can be determined by measuring the pore area of 200 or more open holes from a scanning electron micrograph of the porous film surface, and calculating the mean diameter from the average value for the pore areas according to the following formula (1), assuming the pore shapes to be circular.

$$\text{Mean pore size} = 2 \times \sqrt{(Sa/\pi)} \quad (1)$$

(wherein Sa represents the average value for the pore areas.)

The porosity of the porous polyimide film used for the invention can be determined by measuring the film thickness and mass of the porous film cut out to a prescribed size, and performing calculation from the basis weight according to the following formula (2).

$$\text{Porosity } (\%) = (1 - w/(S \times d \times D)) \times 100 \quad (2)$$

(wherein S represents the area of the porous film, d represents the total film thickness, w represents the measured mass, and D represents the polyimide density, the polyimide density being defined as 1.34 g/cm$^3$.)

For example, the porous polyimide films described in International Patent Publication No. WO2010/038873, Japanese Unexamined Patent Publication No. 2011-219585 and Japanese Unexamined Patent Publication No. 2011-219586 may also be used in the method of the invention.

The cells that have been seeded on the surface of the porous polyimide film can stably grow and proliferate on the surface and/or in the interior of the film. The cells may be in a variety of different forms, depending on the location of growth and proliferation in the film. According to one mode of the invention, growth may be carried out while moving the surface and interior of the porous polyimide film and changing the form, depending on the type of cell.

Naturally, the porous polyimide film to which cells are loaded in the invention is preferably in a state including no cells other than those that are to be loaded, i.e. a sterilized state. The method of the invention preferably includes a step of pre-sterilizing the porous polyimide film. A porous polyimide film has very excellent heat resistance and is lightweight, allows free selection of the shape and size, and is easy to treat for sterilization. Any desired sterilization treatment may be conducted, such as dry heat sterilization, steam sterilization, sterilization with a disinfectant such as ethanol, or electromagnetic wave sterilization using ultraviolet rays or gamma rays.

I. Method of Culturing Bone Marrow Cells

The present invention relates to a method of culturing bone marrow cells which includes applying bone marrow cells to a porous polyimide film and culturing them. The entire content of International Application Number PCT/JP2014/070407 is incorporated herein by reference.

The method of culturing bone marrow cells of the invention includes applying bone marrow cells to a porous polyimide film and culturing them. The method of the invention is characterized by including applying bone marrow cells to a porous polyimide film and culturing the bone marrow cells on the surface or in the interior of the polyimide film.

1. Bone Marrow Cells

Throughout the present specification, "bone marrow cells" refers to cells present in bone marrow. Bone marrow cells include marrow stromal cells, bone marrow-derived blood cell progenitor cells and bone marrow-derived blood cells. Marrow stromal cells are cells that support bone marrow-derived blood cells. Bone marrow-derived blood cell progenitor cells are cells that, upon division and differentiation are capable of differentiating to hematocytes or blood cells. Bone marrow-derived blood cells are blood cells included in bone marrow.

The source of the bone marrow cells to be used for the method of culturing bone marrow cells according to the invention is not particularly restricted so long as the cells are from an animal belonging to the class Mammalia, or mammals, and examples include mice, rats, humans, monkeys, pigs, dogs, sheep and goats.

The bone marrow cells to be used in the method of culturing bone marrow cells according to the invention may be cells harvested from mammalian bone marrow. The harvesting of the bone marrow cells from bone marrow can be carried out using a known method, such as bone marrow puncture or bone marrow flushing. The bone marrow cells to be used for the invention may also be primary cultured cells from cells harvested from mammalian bone marrow.

2. Application of Bone Marrow Cells to Porous Polyimide Film

In the method for culturing bone marrow cells of the invention, there are no particular restrictions on the specific steps for application of the bone marrow cells to the porous polyimide film. It is possible to carry out the steps described throughout the present specification, or to employ any desired method suited for applying bone marrow cells to a film-like support. Application of bone marrow cells to the porous polyimide film in the method of the invention includes, but is not limited to, the following modes.

(A) A mode including a step of seeding bone marrow cells on the surface of a porous polyimide film;

(B) A mode including a step of:

placing a bone marrow cell suspension on the dried surface of a porous polyimide film, allowing it to stand, or moving the porous polyimide film to promote efflux of the liquid, or stimulating part of the surface to cause absorption of the bone marrow cell suspension into the film, and retaining the bone marrow cells in the bone marrow cell suspension inside the film and allowing the water to flow out; and (C) A mode including a step of:

wetting one or both sides of a porous polyimide film with a bone marrow cell culture solution or a sterilized liquid, loading a bone marrow cell suspension into the wetted porous polyimide film, and retaining the bone marrow cells in the bone marrow cell suspension inside the film and allowing the water to flow out.

Mode (A) includes a step of directly seeding bone marrow cells or a bone marrow cell mass on the surface of a porous polyimide film. Alternatively, it includes a mode of placing a porous polyimide film in a bone marrow cell suspension and wetting the bone marrow cell culture solution from the surface of the film.

Bone marrow cells seeded on the surface of a porous polyimide film adhere to the porous polyimide film and infiltrate into the interiors of the pores. Preferably, the bone marrow cells adhere spontaneously to the porous polyimide film without applying any particular exterior physical or chemical force. The bone marrow cells that have been seeded on the surface of the porous polyimide film can stably grow and proliferate on the surface and/or in the interior of the film. The bone marrow cells may be in a variety of different forms, depending on the location of the film used for growth and proliferation.

For mode (B), a bone marrow cell suspension is placed on the dried surface of a porous polyimide film. The porous polyimide film is allowed to stand, or the porous polyimide film is moved to promote efflux of the liquid, or part of the surface is stimulated to cause absorption of the bone marrow cell suspension into the film, so that the bone marrow cell suspension permeates into the film. While it is not our intention to be constrained by theory, this is believed to be due to the properties of each of the surface forms of the porous polyimide film. According to this mode, the bone marrow cells are absorbed and seeded in the locations of the film where the cell suspension has been loaded.

Alternatively, as according to mode (C), after all or a portion of one or both sides of the porous polyimide film has been wetted with the bone marrow cell culture solution or sterilized liquid, the bone marrow cell suspension may be loaded into the wetted porous polyimide film. This will significantly increase the transit rate of the cell suspension.

For example, a method of wetting a portion of the film edges, for the main purpose of preventing fly loss of the film, may be used (hereunder referred to as "single-point wetting method"). The single-point wetting method is nearly the same as the dry method (mode (B)) in which the film essentially is not wetted. However, it is possible that bone marrow cell solution permeation through the film is more rapid at the small wetted portions. There may also be used a method in which all of one or both sides of the porous polyimide film that have been thoroughly wetted (hereunder this will also be referred to as "wet film") is loaded with a bone marrow cell suspension (this will hereunder be referred to as "wet film method"). In this case, the entire porous polyimide film has a greatly increased transit rate for the bone marrow cell suspension.

According to modes (B) and (C), the bone marrow cells in the bone marrow cell suspension are retained in the film, while the water flows out. This allows treatment such as increasing the concentration of bone marrow cells in the bone marrow cell suspension and flowing out of unwanted non-cellular components together with the water.

Mode (A) will also be referred to as "natural seeding", and modes (B) and (C) as "suction seeding".

Preferably, but not restrictively, the viable cells are selectively retained in the porous polyimide film. Thus, according to a preferred mode of the invention, the viable cells are retained in the porous polyimide film, and the dead cells preferentially flow out together with the water.

The sterilized liquid used for mode (C) is not particularly restricted, and may be a sterilized buffering solution or sterilized water. A buffering solution may be, for example, (+) or (−) Dulbecco's PBS, or (+) or (−) Hank's Balanced Salt Solution. Examples of buffering solutions are listed in Table 1 below.

TABLE 1

| Component | Concentration (mmol/L) | Concentration (g/L) |
| --- | --- | --- |
| NaCl | 137 | 8.00 |
| KCl | 2.7 | 0.20 |
| $Na_2HPO_4$ | 10 | 1.44 |
| $KH_2PO_4$ | 1.76 | 0.24 |
| pH (—) | 7.4 | 7.4 |

In the method for culturing bone marrow cells of the invention, application of bone marrow cells to the porous polyimide film further includes a mode of adding cells in a floating state as a suspension together with the porous polyimide film, to adhere the bone marrow cells with the film (entangling). For example, for application of the bone marrow cells to the porous polyimide film in the cell culturing method of the invention, the cell culture medium, the bone marrow cells and one or more of the porous polyimide films may be placed in the cell culturing vessel. When the cell culture medium is a liquid, the porous polyimide film is in a floating state in the cell culture medium. The bone marrow cells can adhere to the porous polyimide film due to the properties of the porous polyimide film. Thus, even with cells that are not suited for natural suspension culture, the porous polyimide film allows culturing in a floating state in the cell culture medium. The bone marrow cells preferably spontaneously adhere to the porous polyimide film. Here, "adhere spontaneously" means that the bone marrow cells are retained on the surface or in the interior of the porous polyimide film without applying any particular exterior physical or chemical force.

In the method for culturing bone marrow cells of the invention, when the porous polyimide film is used in a state suspended in the cell culture medium, two or more fragments of the porous polyimide film may be used. Since the porous polyimide film is a flexible thin-film, using such fragments that are suspended in the culture solution, for example, allows a porous polyimide film with a large surface area to be added into a fixed volume of cell culture medium. In the case of normal culturing, the container base area constitutes the area limit in which cell culture can be accomplished, but with cell culturing using the porous polyimide film of the invention, all of the large surface area of the previously added porous polyimide film constitutes area in which cell culturing can be accomplished. The porous polyimide film allows the cell culture solution to pass through, allowing supply of nutrients, oxygen and the like even into the folded film, for example.

The sizes and shapes of the porous polyimide film fragments are not particularly restricted. The shapes may be as desired, such as circular, elliptical, quadrilateral, triangular, polygonal or string-like.

Because the porous polyimide film used in the method for culturing bone marrow cells of the invention is flexible, it can be used with varying shapes. Instead of a flat form, the porous polyimide film can also be used by working into a three-dimensional shape. For example, porous polyimide films may be: i) folded, ii) wound into a roll, iii) connected as sheets or fragments by a filamentous structure, or iv) bound into a rope, for suspension or fixing in the cell culture medium in the cell culturing vessel. By forming into shapes such as i) to iv), it is possible to place a large amount of porous polyimide films into a fixed volume of cell culture medium, similar to using fragments. Furthermore, since each fragment can be treated as an aggregate, it is possible to aggregate and move the cell masses together, for overall high applicability.

With the same concept as fragment aggregates, two or more porous polyimide films may be used in a layered form either above and below or left and right in the cell culture medium. Layering includes a mode in which portions of the porous polyimide films overlap. Layered culturing allows culturing of cells at high density in a narrow space. It is also possible to further layer a film on a film on which cells are already growing, setting it to create a multilayer of different cell types. The number of layered porous polyimide films is not particularly restricted.

Two or even more forms of the bone marrow cell culturing method of the invention described above may be used in combination. For example, using any of the methods of modes (A) to (C), first the cells may be applied to the porous polyimide film and then the bone marrow cell-adhered porous polyimide film may be used for suspension culture. Alternatively, the step of application to the porous polyimide film may be a combination of two or more of the methods of any of modes (A) to (C).

The porous polyimide film to be used in the method of culturing bone marrow cells according to the invention is a porous polyimide film having two different surface layers (A-surface and B-surface), and a macro-void layer sandwiched between the two surface layers, and when the mean pore size of the holes in the A-surface is smaller than the mean pore size of the holes in the B-surface, the bone marrow cells may be either applied from the A-surface or applied from the B-surface. The bone marrow cells are preferably applied from the A-surface.

In the method of culturing bone marrow cells of the invention, preferably the bone marrow cells grow and proliferate on the surface or in the interior of the porous polyimide film.

In the method for culturing bone marrow cells of the invention, the bone marrow cell culturing system and culturing conditions may be set as appropriate according to the type of cells used. A person skilled in the art may carry out culturing of cells suited for the porous polyimide film, using any publicly known method. The cell culture medium may also be prepared as appropriate for the type of cells.

The cell culture medium to be used in the method for culturing bone marrow cells of the invention may be in any form such as a liquid medium, semi-solid medium or solid medium. Also, a liquid medium in droplet form may be sprayed into the cell culturing vessel to contact the medium with the cell-supporting porous polyimide film.

The cell culture using a porous polyimide film may also be combined with another suspension culture support such as a microcarrier, cellulose sponge or the like.

The method for culturing bone marrow cells of the invention is not particularly restricted in terms of the form and scale of the system used for the culturing, and any scale from cell culturing dish to a flask, plastic bag, test tube or large tank may be used, as appropriate. These include, for example, Cell Culture Dish by BD Falcon, and Nunc Cell Factory by Thermo Scientific. By using a porous polyimide film according to the invention, it has become possible to carry out culturing even of cells that have not been capable of natural suspension culture, using an apparatus intended for suspension culture, in a state similar to suspension culturing. The apparatus for suspension culture that is used may be, for example, a spinner flask or rotating culturing flask by Corning, Inc. As an environment allowing a similar function to be obtained, there may be used a hollow fiber culturing system such as the FiberCell® System by Veritas.

The culturing in the method for culturing bone marrow cells of the invention may be carried out in a manner with continuous circulation such as continuous addition and recovery of the medium on the porous polyimide film, or exposure of the porous polyimide film sheet to air using an open apparatus.

In the method for culturing bone marrow cells of the invention, cell culturing may be carried out in a system in which a cell culture medium is continuously or intermittently supplied to a cell culturing vessel from cell culture medium supply means installed outside of the cell culturing vessel. The system may be such that the cell culture medium is circulated between the cell culture medium supply means and the cell culturing vessel.

When the cell culturing is carried out in a system in which the cell culture medium is continuously or intermittently supplied to the cell culturing vessel from cell culture medium supply means installed outside of the cell culturing vessel, the system may be a cell culturing apparatus including a culturing unit which is the cell culturing vessel, and a culture medium-supply unit which is the cell culture medium supply means, wherein the culturing unit is a culturing unit that houses one or more porous polyimide films to support cells, and that comprises a culture medium supply port and a culture medium discharge port, and the culture medium-supply unit is a culture medium-supply unit comprising a culture medium housing vessel, a culture medium supply line, and a liquid conveyance pump that conveys the medium continuously or intermittently through the culture medium supply line, the first end of the culture medium supply line contacting the medium in the culture medium housing vessel, and the second end of the culture medium supply line being in communication with the culturing unit interior via the culture medium supply port of the culturing unit.

In the cell culturing apparatus, the culturing unit may be a culturing unit that does not comprise an air supply port, an air discharge port and an oxygen exchange membrane, or it may be a culturing unit that comprises an air supply port and an air discharge port, or an oxygen exchange membrane. Even if the culturing unit does not comprise an air supply port, an air discharge port and an oxygen exchange membrane, the oxygen, etc. necessary for cell culturing is adequately supplied to the cells through the medium. Furthermore, in the cell culturing apparatus described above, the culturing unit may further comprise a culture medium discharge line, the first end of the culture medium discharge line being connected to the culture medium housing vessel, the second end of the culture medium discharge line being in communication with the culturing unit interior via the culture medium discharge port of the culturing unit, and the medium being able to circulate through the culture medium-supply unit and the culturing unit.

3. Differentiation of Bone Marrow Cells to Hematocytes

The invention also relates to a method of culturing bone marrow cells that further includes causing differentiation of bone marrow cells to hematocytes by culturing.

Throughout the present specification, hematocytes include leukocytes such as neutrophils, eosinophils, basophils, lymphocytes, monocytes and macrophages, and erythrocytes, platelets, mast cells and dendritic cells, as well as precursors of the foregoing.

When bone marrow cells are applied to a porous polyimide film and culturing is continued, some of the bone marrow cells can be induced to differentiate to hematocytes. While it is not our intention to be constrained by theory, since the spatial structure of a porous polyimide film approximates the spatial structure of bone marrow, cells with differentiating characteristics similar to bone marrow become arranged and proliferate in a manner following the spatial structure of the porous polyimide film. By thus approximately reproducing the in vivo structure of bone marrow in the porous polyimide film, differentiation to hematocytes is induced. Throughout the present specification, inducing differentiation to hematocytes by approximately reproducing the in vivo structure of bone marrow in the porous polyimide film will be referred to as being differentiation from bone marrow cells to hematocytes in a manner specific to the spatial structure of the porous polyimide film.

In the method of culturing bone marrow cells of the invention, bone marrow cells may be applied to a porous polyimide film and then a differentiation-inducing accelerating substance added, to accelerate differentiation from the bone marrow cells to hematocytes in a manner specific to the spatial structure of the porous polyimide film. The differentiation-inducing accelerating substance may be a known substance used as appropriate for the purpose, examples of which include colony-stimulating factor, granulocyte colony stimulating factor, stem-cell factor, stem cell growth factor-α, erythropoietin, thrombopoietin and interleukin, although there is no limitation to these. In the method of the invention, a single type of differentiation-inducing accelerating substance may be used alone, or a combination of several different differentiation-inducing accelerating substances may be used.

The invention also relates to a method of preparing hematocytes that includes recovering hematocytes obtained by the method of culturing bone marrow cells described above.

II. Method of Culturing Bone Marrow Cells in Which Bone Marrow Cells are Applied to a Porous Polyimide Film and Cultured, in Two Stages.

The invention also relates to a method of culturing bone marrow cells including:

(1) a step of applying a first cell group to a porous polyimide film and culturing it, and (2) a step of applying a second cell group to the porous polyimide film after the culturing in step (1), and culturing it, wherein the second cell group consists of bone marrow cells.

The type of first cell group may be any of type of cells, and for example, they may be selected from the group consisting of animal cells, insect cells, plant cells, yeast cells and bacteria. Animal cells, for the purpose of the present specification, are largely divided into cells from animals belonging to the subphylum Vertebrata, and cells from non-vertebrates (animals other than animals belonging to the subphylum Vertebrata).

There are no particular restrictions on the source of the animal cells, for the purpose of the present specification. Preferably, they are cells from an animal belonging to the subphylum Vertebrata. The subphylum Vertebrata, for the purpose of the present specification, includes the superclass Agnatha and the superclass Gnathostomata, the superclass Gnathostomata including the class Mammalia, the class Aves, the class Amphibia and the class Reptilia. Preferably, they are cells from an animal belonging to the class Mammalia, generally known as mammals. Mammals, for the purpose of the present specification, are not particularly restricted but include, preferably, mice, rats, humans, monkeys, pigs, dogs, sheep and goats.

There are also no particular restrictions on sources of plant cells, for the purpose of the present specification. Suitable cells are from plants including bryophytes, pteridophytes and spermatophytes.

Plants from which spermatophyte cells are derived, for the purpose of the present specification, include both monocotyledons and dicotyledons. While not restrictive, monocotyledons include Orchidaceae plants, Poaceae plants (rice, corn, barley, wheat, sorghum and the like) and Cyperaceae plants. Dicotyledons include plants belonging to many subclasses including the subclass Chrysanthemum, the subclass Magnoliidae and the subclass Rosidae.

For the purpose of the present specification, algae may be considered cell-derived organisms. These include different groups, from the eubacteria Cyanobacteria (blue-green algae), to eukaryotic monocellular organisms (diatoms, yellow-green algae, dinoflagellates and the like) and multicellular marine algae (red algae, brown algae and green algae).

There are no particular limitations on the types of archaebacteria or bacteria for the purpose of the present specification. Archaebacteria are composed of groups comprising methanogenic bacteria, extreme halophilic bacteria, thermophilic acidophilic bacteria, hyperthermophilic bacteria and the like. Bacteria are selected from the group consisting of, for example, lactic acid bacteria, *E. coli, Bacillus subtilis* and cyanobacteria.

The types of animal cells or plant cells that may be used for the method of culturing bone marrow cells of the invention are not particularly restricted, but are preferably selected from the group consisting of pluripotent stem cells, tissue stem cells, somatic cells and germ cells.

Throughout the present specification, the term "pluripotent stem cells" is intended as a comprehensive term for stem cells having the ability to differentiate into cells of a variety of tissues (pluripotency). While not a restriction, pluripotent stem cells include embryonic stem cells (ES cells), induced pluripotent stem cells (iPS cells), embryonic germ cells (EG cells) and germ stem cells (GS cells). They are preferably ES cells or iPS cells. Particularly preferred are iPS cells, which are free of ethical problems, for example. The pluripotent stem cells used may be any publicly known ones, and for example, the pluripotent stem cells described in International Patent Publication No. WO2009/123349 (PCT/JP2009/057041) may be used.

Throughout the present specification, the term "tissue stem cells" refers to stem cells that are cell lines capable of differentiation but only to limited specific tissues, though having the ability to differentiate into a variety of cell types (multipotency). For example, hematopoietic stem cells in the bone marrow are the source of blood cells, while neural stem cells differentiate into neurons. Additional types include hepatic stem cells from which the liver is formed and skin stem cells that form skin tissue. Preferably, the tissue stem cells are selected from among mesenchymal stem cells, hepatic stem cells, pancreatic stem cells, neural stem cells, skin stem cells and hematopoietic stem cells.

Throughout the present specification, the term "somatic cells" refers to cells other than germ cells, among the cells composing a multicellular organism. In sexual reproduction, these are not passed on to the next generation. Preferably, the somatic cells are selected from among hepatocytes, pancreatic cells, muscle cells, bone cells, osteoblasts, osteoclasts, chondrocytes, adipocytes, skin cells, fibroblasts, pancreatic cells, renal cells and lung cells, or blood cells such as lymphocytes, erythrocytes, leukocytes, monocytes, macrophages or megakaryocytes.

Throughout the present specification, the term "germ cells" refers to cells having the role of passing on genetic information to the succeeding generation in reproduction. These include, for example, gametes for sexual reproduction, i.e. the ova, egg cells, sperm, sperm cells, and spores for asexual reproduction.

For the purpose of the present specification, the cells may also be selected from the group consisting of sarcoma cells, established cell lines and transformants. The term "sarcoma" refers to cancer occurring in non-epithelial cell-derived connective tissue cells, such as the bone, cartilage, fat, muscle or blood, and includes soft tissue sarcomas, malignant bone tumors and the like.

Sarcoma cells are cells derived from sarcoma. The term "established cell line" refers to cultured cells that are maintained in vitro for long periods and reach a stabilized character and can be semi-permanently subcultured. Cell lines derived from various tissues of various species including humans exist, such as PC12 cells (from rat adrenal medulla), CHO cells (from Chinese hamster ovary), HEK293 cells (from human embryonic kidney), HL-60 cells from (human leukocytes) and HeLa cells (from human cervical cancer), Vero cells (from African green monkey kidney epithelial cells), MDCK cells (from canine renal tubular epithelial cells) and HepG2 cells (from human hepatic cancer). The term "transformants" refers to cells with an altered genetic nature by extracellularly introduced nucleic acid (DNA and the like). Suitable methods are known for transformation of animal cells, plant cells and bacteria.

In the method of culturing bone marrow cells of the invention, the first cell group preferably consists of bone marrow cells.

The method of applying the first cell group to the porous polyimide film may be carried out in the same manner as the method of applying the bone marrow cells to the porous polyimide film.

The method of culturing bone marrow cells in which bone marrow cells are applied to and cultured on a porous polyimide film in two stages, includes a step in which the first cell group is applied to the porous polyimide film and cultured, after which the second cell group is applied to the porous polyimide film and cultured, where the second cell group consists of bone marrow cells.

In the method of culturing bone marrow cells in which bone marrow cells are applied to and cultured on a porous polyimide film in two stages, the bone marrow cells may be differentiated to hematocytes by the method described above, after application and culturing of the second cell group. This may be followed by an additional step of recovering the hematocytes.

For example, after ordinary bone marrow cells as the first cell group have been applied to and cultured on the porous polyimide film, GFP transgenic mouse-derived bone marrow cells, as the second cell group, may be applied to and cultured on the porous polyimide film. After confirming the cells visualized by GFP, differentiation from the bone marrow cells to hematocytes may then be monitored.

III. Kit for Use in Method of Culturing Bone Marrow Cells

The present invention also relates to a kit for use in the method of culturing bone marrow cells of the invention, the kit including a porous polyimide film.

The kit of the invention may include constituent elements necessary for cell culturing in addition to the porous polyimide film, as appropriate. This includes, for example, the cells to be applied to the porous polyimide film, the cell culture medium, the continuous culture medium-supply apparatus, the continuous culture medium-circulating apparatus, the scaffold or module for support of the porous polyimide film, the cell culturing apparatus, and the kit instruction manual.

While not restrictive, one mode includes a package containing either one or a plurality of sterilized porous polyimide films stored in a transparent pouch, in a form allowing their use for cell culturing, or a kit having a sterile liquid encapsulated together with a porous polyimide film in the same pouch, in the form of an integrated film/liquid allowing efficient suction seeding.

IV. Use of Porous Polyimide Film for Method of Culturing Bone Marrow Cells

The invention also relates to use of a porous polyimide film for the aforementioned method of culturing bone marrow cells.

V. Porous Polyimide Film for Healing of a Bone Injury Site.

The invention also relates to a porous polyimide film for healing of bone injury sites.

1. Bone Injury

Throughout the present specification, "bone injury" refers to a state of damage to bone tissue caused by trauma, fatigue, disease or the like, and it includes, for example, a state of damage only to the surface of bone tissue, as well as fracture and bone loss. Throughout the present specification, "fracture" includes complete fracture where the bone has lost complete continuity, and incomplete fracture where the bone has not lost complete continuity. Modes of fracture include closed fracture (simple fracture) in which the fracture site is not released out of the body, open fracture (complex fracture) in which the fracture site is released out of the body, single fracture in which one bone is disjoined at only one location, and compound fracture (double fracture) in which one bone is disjoined at multiple locations. The porous polyimide film of the invention may be applied to any of these modes of fracture.

Throughout the present specification, "healing of a bone injury site" means partial or complete improvement, repair or restoration of the damaged state of a site of bone injury. The term "healing of a fracture site" means partial or complete improvement, repair or restoration of a site where bone has been disjoined or lost. Also, "accelerate healing of a bone injury" means to shorten the period for improvement, repair or restoration of the state of damage at a site where bone has been damaged, or to enlarge the area of improvement, repair or restoration of the damaged state.

The index for healing or acceleration of healing at a bone injury site may be adhesion of disjoined bone, decrease in the area or volume of bone loss, bone mineral density (BMD), bone mineral content (BMC), bone mass or new bone formation volume (BV).

2. Treatment of Porous Polyimide Film Surface

The porous polyimide film of the invention may have its surface partially or completely treated by a step that modifies its physical properties. The step of modifying the physical properties of the surface of the porous polyimide film may be selected as any desired step suited for the purpose so long as it does not interfere with healing of the bone injury site, and for example, it may be a step of alkali treatment or calcium treatment of the surface of the porous polyimide film, a step of covering with a biocompatible material, or a combination of any of the foregoing.

A step of alkali treatment of the surface of the porous polyimide film may be, for example, a step of applying an alkaline substance such as sodium hydroxide or potassium hydroxide to the surface of the porous polyimide film, and modifying the physical properties of the surface of the porous polyimide film, although this is not limitative.

A step of calcium treatment of the surface of the porous polyimide film may be, for example, applying a calcium-containing substance such as calcium chloride, calcium phosphate or calcium fluoride to the surface of the porous polyimide film, and modifying the physical properties of the surface of the porous polyimide film, although this is not limitative.

A step of alkali treatment of the surface of the porous polyimide film may also be followed by calcium treatment of the surface of the porous polyimide film.

Biocompatible materials that may be used in a step of covering the surface of the porous polyimide film with a biocompatible material include collagen, fibronectin, laminin, polylysine, polylactide, polyglycolide, polycaprolactone, polyhydroxybutyrate, polylactide-co-caprolactone, polycarbonate, biodegradable polyurethane, polyether ester, polyesteramide, hydroxyapatite, collagen/β-TCP (β-tricalcium phosphate) complex, and combinations of the foregoing, with no limitation to these. The method of covering with a biocompatible material may be a method known to those skilled in the art, used as appropriate.

After alkali treatment and/or calcium treatment of the surface of the porous polyimide film, the surface may be further covered with the biocompatible material.

3. Porous Polyimide Film with Cells Supported Beforehand

The porous polyimide film of the invention may be one on which cells have been supported beforehand. The porous polyimide film of the invention has a feature whereby it can hold and grow cells inside its characteristic spatial structure. By supporting cells suited for a given purpose on the porous polyimide film and applying them to a bone injury site, it is possible to accelerate healing of the bone injury site.

Although any desired method may be used as the method of supporting the cells on the porous polyimide film according to the invention, the following method may be mentioned as an example.

(A) A mode including a step of seeding cells on the surface of a porous polyimide film;

(B) A mode including a step of: placing a cell suspension on the dried surface of the porous polyimide film, allowing it to stand, or moving the porous polyimide film to promote efflux of the liquid, or stimulating part of the surface to cause absorption of the cell suspension into the film, and retaining the cells in the cell suspension inside the film and allowing the water to flow out; and (C) A mode including a step of:

wetting one or both sides of the porous polyimide film with a cell culture solution or a sterilized liquid, loading a cell suspension into the wetted porous polyimide film, and retaining the cells in the cell suspension inside the film and allowing the water to flow out.

Cells seeded on the surface of the porous polyimide film of the invention adhere to the porous polyimide film and infiltrate into the interiors of the pores. Preferably, the cells adhere spontaneously to the porous polyimide film without applying any particular exterior physical or chemical force. The cells that have been seeded on the surface of the porous polyimide film can stably grow and proliferate on the surface and/or in the interior of the film. The cells may be in a variety of different forms, depending on the location of the film used for growth and proliferation.

The porous polyimide film of the invention is a porous polyimide film having two different surface layers (A-surface and B-surface), and a macro-void layer sandwiched between the two surface layers, and when the mean pore size of the holes in the A-surface is smaller than the mean pore size of the holes in the B-surface, the cells may be applied from the A-surface or applied from the B-surface. The cells are preferably applied from the A-surface.

After the cells have been seeded on the surface of the porous polyimide film of the invention, the cells may be cultured on the porous polyimide film, according to the purpose. The cultured cells are supported on the porous polyimide film.

There are no particular restrictions on the type of cells to be supported on the porous polyimide film of the invention and any desired type of cells may be used, but it is generally preferred to use cells from an animal belonging to the class Mammalia, known as mammals. Mammals are not particularly restricted but include, preferably, mice, rats, humans, monkeys, pigs, dogs, sheep and goats.

The type of animal cells to be supported on the porous polyimide film of the invention is not restricted but is preferably selected from the group consisting of pluripotent stem cells, tissue stem cells, somatic cells and combinations of the foregoing.

The bone marrow cells to be supported on the porous polyimide film of the invention may be cells harvested from mammalian bone marrow. The harvesting of the bone marrow cells from bone marrow can be carried out using a known method, such as bone marrow puncture or bone marrow flushing. The bone marrow cells to be supported on the porous polyimide film of the invention may also be primary cultured cells from cells harvested from mammalian bone marrow.

The porous polyimide film of the invention has a characteristic spatial structure whose form morphologically approximates the structure of bone marrow. The present inventors have found that when bone marrow cells are seeded and cultured on a porous polyimide film, it is possible to cause proliferation of CD45-positive cells, and a cell mass is produced having differentiating characteristics similar to bone marrow, while following the spatial structure of the porous polyimide film. The porous polyimide film that can be used for the invention may be one on which bone marrow cells have been seeded and cultured. A publicly known medium may be used as appropriate for the culturing.

One mode of the invention is a porous polyimide film supporting bone marrow cells harvested from a target for bone injury healing. By using such a porous polyimide film for bone injury healing, it is possible to not only provide structural supplementation at the bone injury site, but also to restore the bone function, including hematopoiesis.

The method used to support the cells on the porous polyimide film of the invention may also be a method including the following steps, for example.

(1) A step of applying a first cell group to a porous polyimide film and culturing it, and (2) a step of applying a second cell group to the porous polyimide film after the culturing in step (1), and culturing and supporting the cells, wherein the second cell group consists of bone marrow cells.

In this cell supporting method, the type of first cell group may be any type of cells, and for example, they may be selected from the group consisting of animal cells, insect cells, plant cells, yeast cells and bacteria. Animal cells are largely divided into cells from animals belonging to the subphylum Vertebrata, and cells from non-vertebrates (animals other than animals belonging to the subphylum Vertebrata). The first cell group preferably consists of bone marrow cells.

4. Porous Polyimide Film for Healing of a Bone Injury Site

The porous polyimide film of the invention may be applied to an affected area of bone injury to heal the bone injury site.

The porous polyimide film of the invention has high heat resistance and flexibility and also excellent shapeability freedom, and it can therefore be cut, molded or worked into any desired shape to match the condition of the affected area of bone injury.

Any desired method suited for the purpose may be employed to apply the porous polyimide film of the invention to an affected area of bone injury, but preferably the porous polyimide film is transplanted into the body in contact with the affected area of bone injury. The porous polyimide film may be placed in contact with the entire affected area of bone injury, or the porous polyimide film may be placed in contact with a portion of the affected area of the bone injury. When the porous polyimide film of the invention is a porous polyimide film with a multilayer structure having two different surface layer sides and a macro-void layer, it is preferably used by being transplanted into the body so that of the two different surface layers, the surface with the smaller mean pore size is in contact with the affected area of bone injury.

The porous polyimide film of the invention may also be effectively used for sites with extensive bone loss or sites with complex fracturing, for which conventional methods have not been applicable. The porous polyimide film of the invention may be applied so as to cover all or a portion of the affected area of bone injury, and there is no particular need for the porous polyimide film to be anchored with another material. Depending on the purpose, however, suture thread, staples, biocompatible screws or the like may be used to anchor the porous polyimide film in the biological tissue.

VI. Kit for Healing of Bone Injury Site

The present invention further relates to a kit for healing of a bone injury site, the kit including the porous polyimide film described above. The kit of the invention may include, in addition to the porous polyimide film, also the materials necessary for bone injury healing surgery, and an instruction manual for the kit.

While not restrictive, one mode includes a package containing either one or a plurality of sterilized porous polyimide films stored in a transparent pouch, in a form allowing their use for bone injury healing, or a kit having a sterile liquid encapsulated together with the porous polyimide film in the same pouch, in the form of an integrated film/liquid allowing efficient cell seeding.

VII. Use of Porous Polyimide Film for Healing of Bone Injury

The invention also relates to use of the aforementioned porous polyimide film for healing of a bone injury.

VIII. Method for Producing Porous Polyimide Film for Healing of Bone Injury Site The present invention further relates to a method for producing a porous polyimide film for healing of a bone injury site, the method including supporting bone marrow cells on a porous polyimide film. The bone marrow cells used may be ones harvested from the target of bone injury site healing.

IX. Method of Healing Bone Injury Site

The present invention further relates to a method of healing a bone injury site that includes applying the aforementioned porous polyimide film to a bone injury site.

The present invention will now be explained in greater detail by examples. It is to be understood, however, that the invention is not limited to these examples. A person skilled in the art may easily implement modifications and changes to the invention based on the description in the present specification, and these are also encompassed within the technical scope of the invention. Unless otherwise specified, the term "porous polyimide film" refers to a porous polyimide film with a total film thickness of 25 μm and a porosity of 73%. Each porous polyimide film had at least two different surface layers (A-surface and B-surface), and a macro-void layer sandwiched between the two surface layers. The mean pore size of the holes in the A-surface was 6 μm, and the mean pore size of the holes in the B-surface was 46 μm.

The porous polyimide films used in the following examples were prepared by forming a polyamic acid solution composition including a polyamic acid solution obtained from 3,3',4,4'-biphenyltetracarboxylic dianhydride (s-BPDA) as a tetracarboxylic acid component and 4,4'-diaminodiphenyl ether (ODA) as a diamine component, and polyacrylamide as a coloring precursor, and performing heat treatment at 250° C. or higher.

EXAMPLES

Example 1

Figure 2:
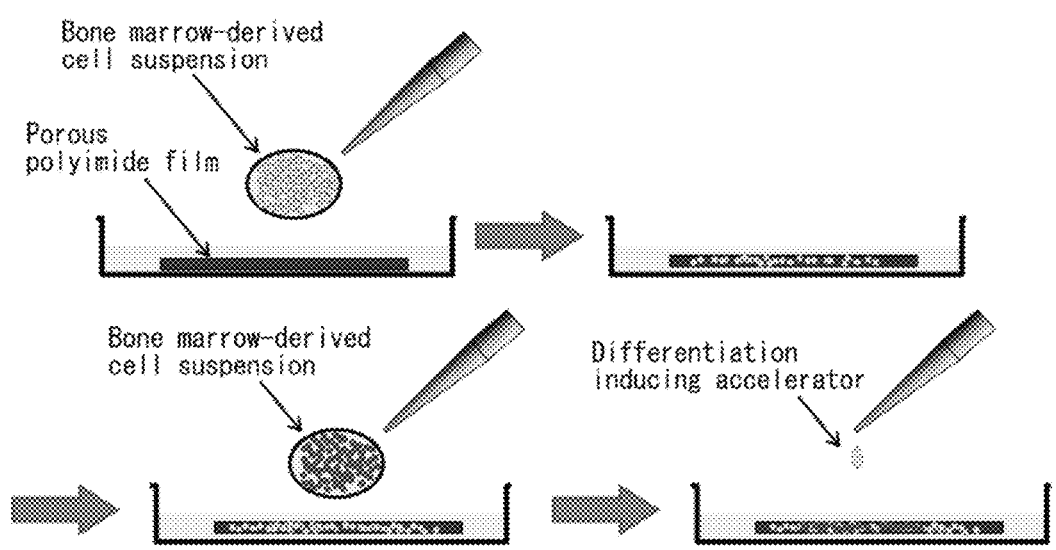
FIG. 2 is a conceptual drawing of bone marrow cell culturing. Cells harvested from bone marrow are seeded and cultured on a porous polyimide film placed in a culturing vessel, after which cells harvested from the same bone marrow are seeded. After further culturing, the cells become fixed on the porous polyimide film and are analyzed by staining or the like. A differentiation-inducing stimulant may also be used.
Figure 3:
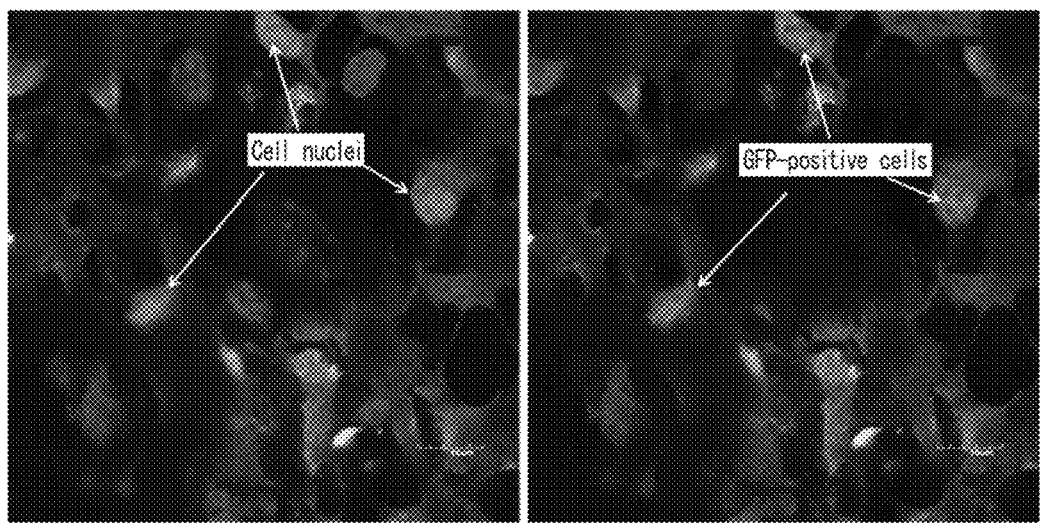
FIG. 3 shows the results of culturing cells harvested from mouse bone marrow, using a porous polyimide film. The upper panel shows a porous polyimide film-fixed image after 7 days of additional culturing (blue: nuclei, green: GFP), while the lower panel shows the B-surface large hole structure and CD45-positive cells (blue: nuclei, green: GFP, red: CD45).
Figure 3:
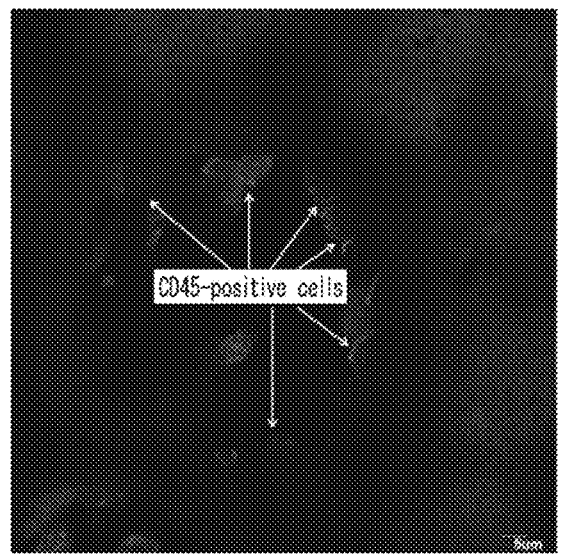

The femora and tibia of 11- to 14-week-old male C57BL/6 mice were extracted, the mesiodistal epiphysis portions were excised, a 10% FBS-containing DMEM solution was used for rinsing, and the bone marrow was harvested. The cell count was $5.0 \times 10^6$. The cells were seeded from the A-surface of a dry heat-sterilized 1 cm-square porous polyimide film, with the A-surface facing upward (FIG. 2). After 5 days of culturing, the medium was exchanged and culturing was continued for 2 days. A second seeding from GFP transgenic mice of the same species, age and gender was performed on a porous polyimide film sheet growing cells that had already been cultured for 7 days, by the same method as described above. After an additional 7 days of culturing, a 4% formalin solution was used to fix the cells, and the specimen was analyzed by immunostaining. GFP positive cells were observed in the fixed specimen, while aggregates of CD45-positive cells were observed around the large hole structure of the B-surface of the porous polyimide film (FIG. 3).

Example 2

Figure 4:
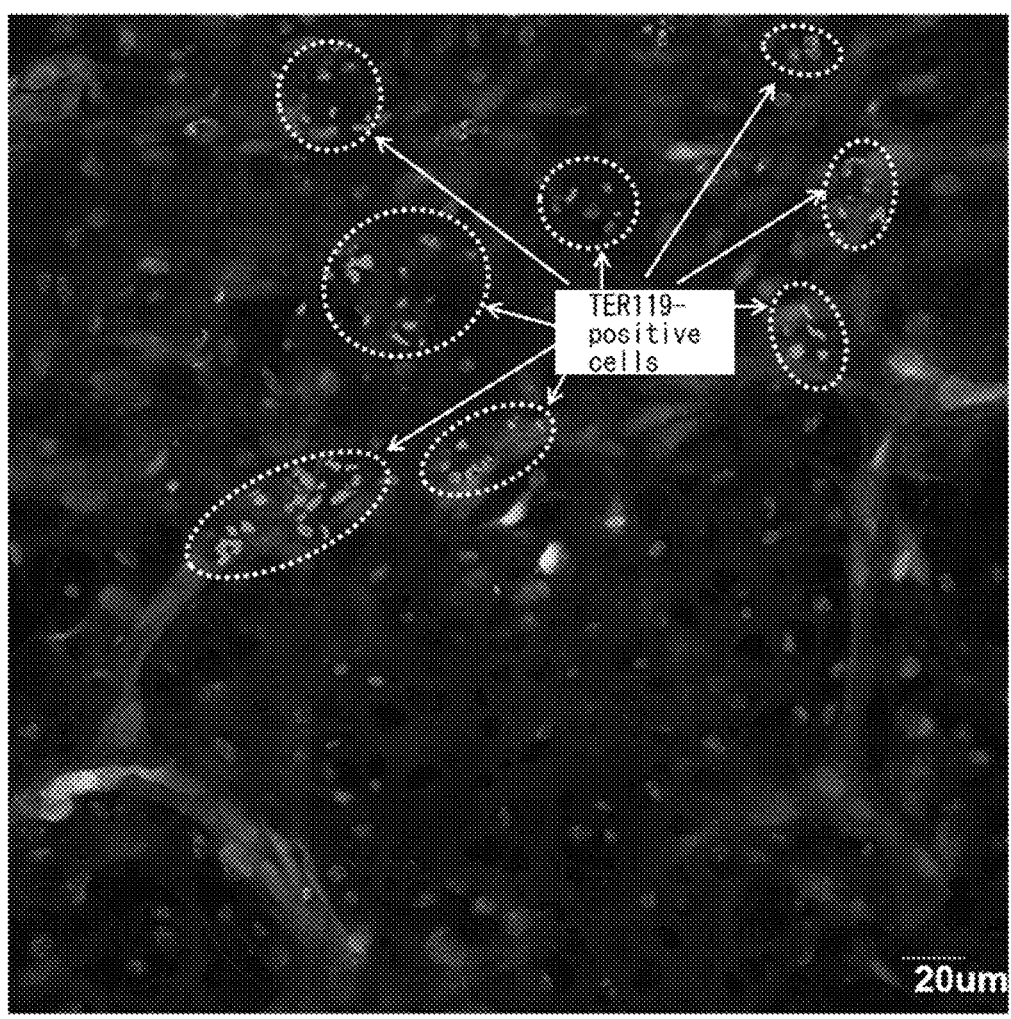
FIG. 4 shows the results of twice seeding bone marrow-derived cells, and then inducing differentiation by erythropoietin. Shown is a fluorescent microscope image taken 24 hours after having completed 7 days of culturing following the second seeding and added 5 units of erythropoietin.
Figure 5:
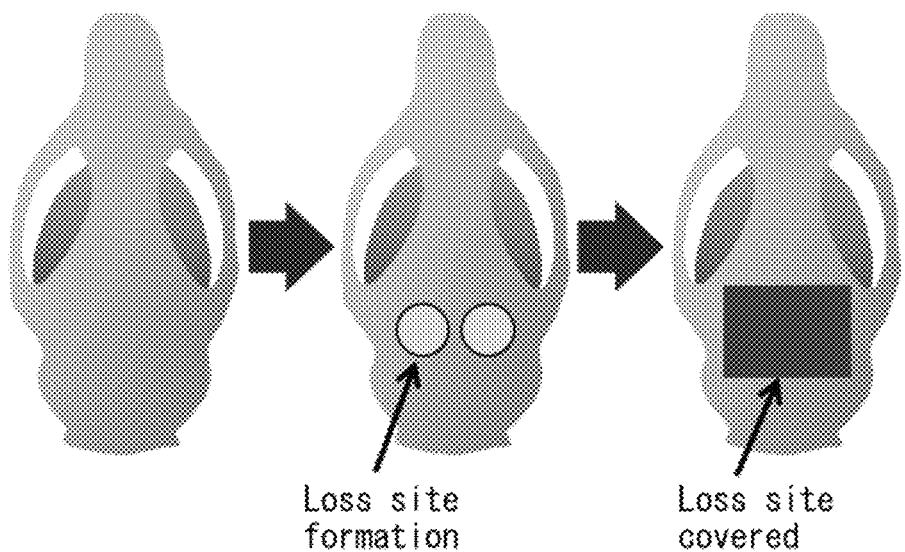
FIG. 5 shows a rat cranial bone loss model.
Figure 6:
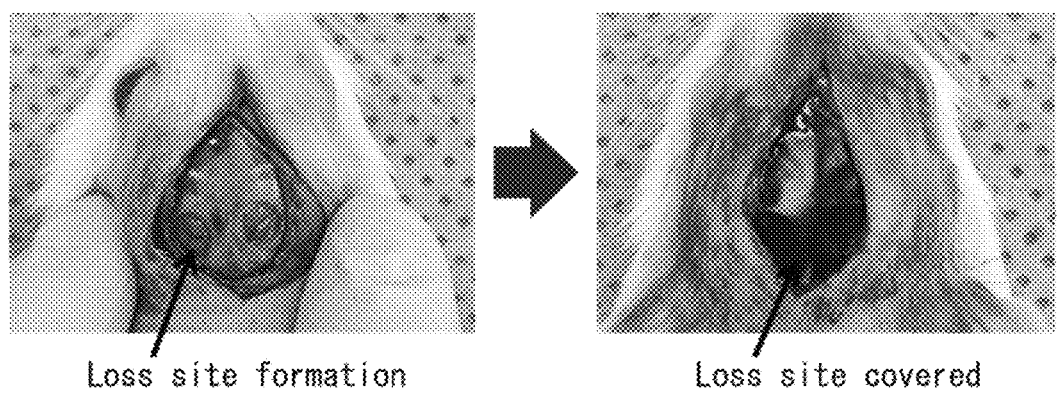
FIG. 6 shows photographs of a technique for covering a site of loss with a porous polyimide film sheet, in a rat cranial bone loss model.

Seeding of bone marrow-derived cells was carried out twice by the same method as in Example 1. Upon 7 days of culturing after the second seeding, erythropoietin was added at 1 unit, 2 units and 5 units per ml. While there was no change in the erythropoietin-free control group, in the erythropoietin-added group the proerythroblast cells (TER119 positive) were observed to form aggregates at each location in a structure-specific manner, depending on the time and volume (FIG. 4).

Example 3

Figure 7:
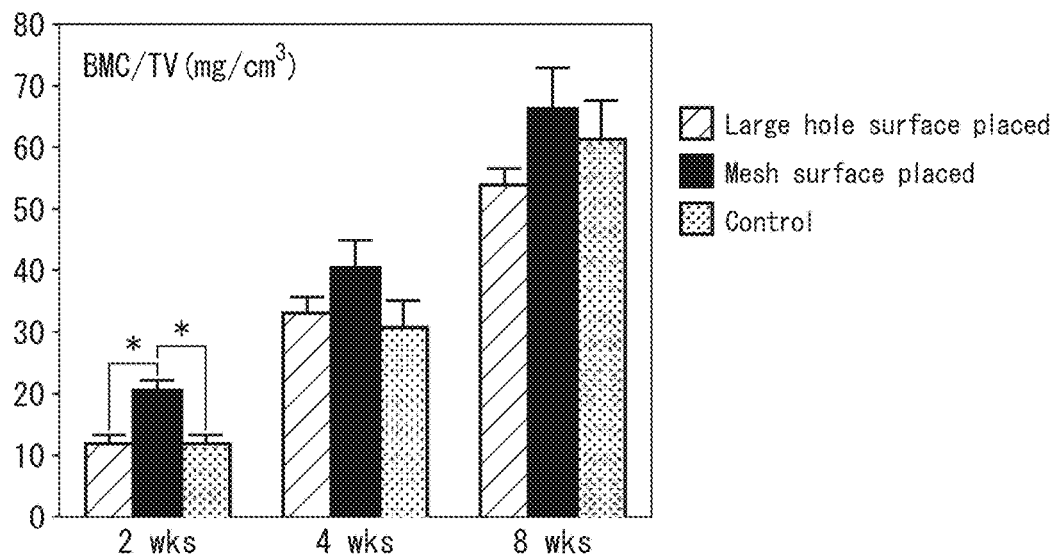
FIG. 7 shows healing of a bone injury, after having applied a porous polyimide film to a bone injury site in a rat cranial bone loss model.

After general anesthesia of 9-week-old LEW rats with 2-3% isoflurane, they were subjected to infiltration anesthesia in the operating field, with 1/10,000 epinephrine-containing lidocaine. A region wider than the incision site was shaved, and then an incision was made at the top of the head on a straight line up to the subperiosteum, for sufficient delineation of the operating field. After detaching the dermal periosteal flap and exposing the parietal bone, a trephine bur was used to form two 4 mm-diameter circular bone loss sections under poured sterile physiological saline. After covering the loss section with a sterilized porous polyimide film, the dermal periosteal flap was reinstated and sutured with a nylon thread. The mesh surface (A-surface) of a porous polyimide film was placed in the wound area to prepare one model, and the large-hole surface (B-surface) was placed to prepare another model. After 2 weeks, 4 weeks and 8 weeks, the state of healing of the loss section was measured. The measured parameters were bone mineral density (BMD) ($mg/cm^3$), bone mineral content (BMC) (mg), new bone formation volume (BV) ($cm^3$), set ROI volume (TV) ($cm^3$), new bone formation percentage (BV/TV) (%) and clinical BMD (BMC/TV) ($mg/cm^3$). As regards early osteogenesis in the mesh surface-placed model, it was confirmed that the model in which the mesh surface had been placed in the wound area had significantly accelerated osteogenesis. The results are shown in FIG. 7. In FIG. 7, the control group is the group without covering of the bone loss section with a porous polyimide film.

Example 4

Figure 8:
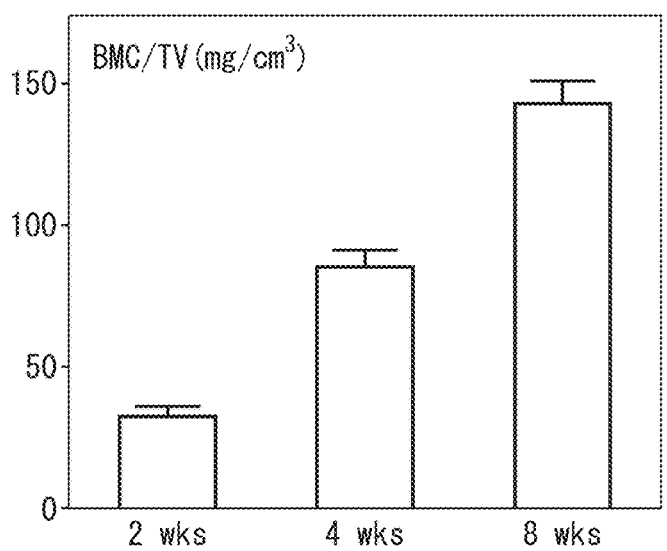
FIG. 8 shows healing of a bone injury, after having applied a porous polyimide film supporting bone marrow cells by single seeding and culturing, to a bone injury site in a rat cranial bone loss model.

After harvesting femora and tibia of 8-week-old GFP transgenic rats and cutting off both ends of each bone, bone marrow cell masses were harvested by flushing with 10% FBS-added DMEM medium. The cell masses were pulverized by pipetting, and $1.0 \times 10^6$ bone marrow cells were seeded on the mesh surface (A-surface) of a 1.5 cm-square porous polyimide film and stationary cultured for 5 days in DMEM medium containing 10% FBS. On the 6th day, the cell-adhered porous polyimide film was rinsed with phosphate buffer and further cultured for 1 day, after only changing the medium to DMEM. After general anesthesia of 9-week-old nude rats with 2-3% isoflurane, they were subjected to infiltration anesthesia in the field of operation, with 1/10,000 epinephrine-containing lidocaine. A region wider than the incision site was shaved, and then an incision was made at the top of the head on a straight line up to the subperiosteum, for sufficient delineation of the operating field. After detaching the dermal periosteal flap and exposing the parietal bone, a trephine bur was used to form two 4 mm-diameter circular bone loss sections under poured sterile physiological saline. The loss section was covered by the porous polyimide film on which the cells had been adhered and then cultured, in a manner so as to place the mesh surface (A-surface) in the wound area. After 2 weeks, 4 weeks and 8 weeks, the condition of healing of the loss section was measured, and healing of the wound area was periodically confirmed. The results are shown in FIG. 8.

Example 5

Figure 9:
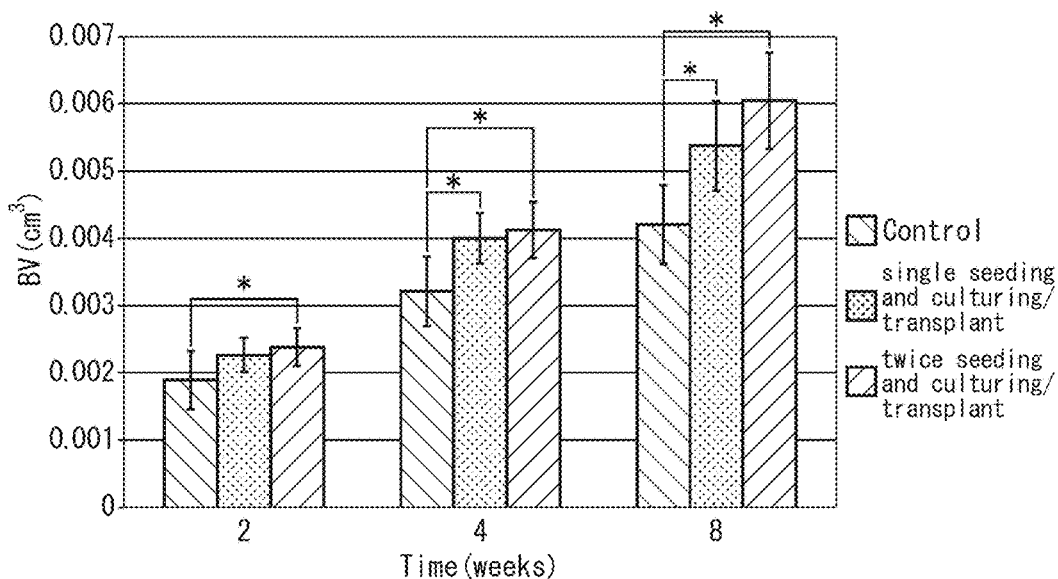
FIG. 9 shows time-dependent change in new bone formation volume (BV) after application of a porous polyimide film supporting bone marrow cells by single or twice seeding and culturing, to a bone injury site in a rat cranial bone loss model.
Figure 10:
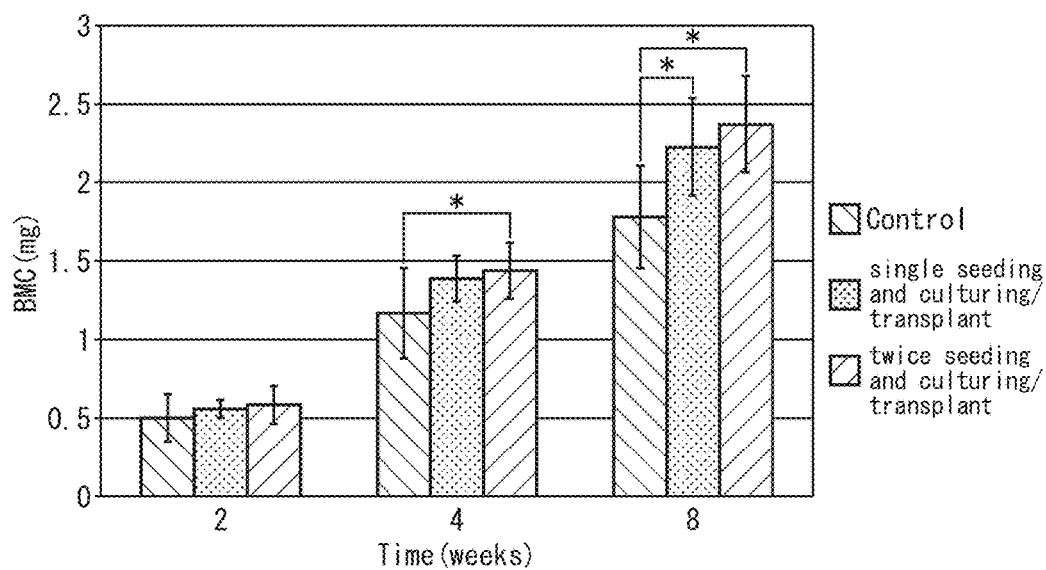
FIG. 10 shows time-dependent change in bone mineral content (BMC) after application of a porous polyimide film supporting bone marrow cells by single or twice seeding and culturing, to a bone injury site in a rat cranial bone loss model.
Figure 11:
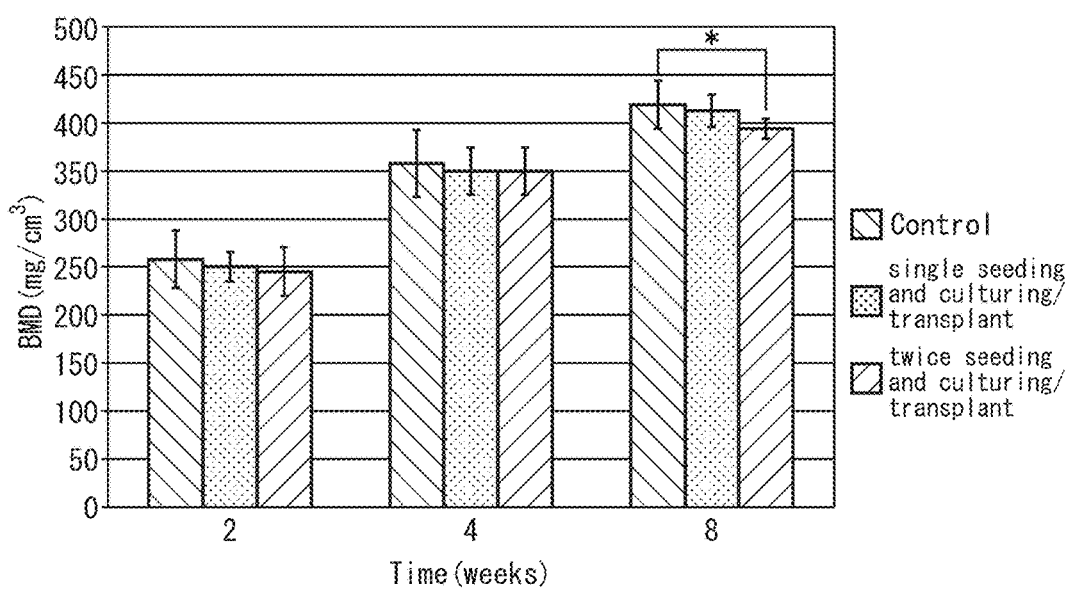
FIG. 11 shows time-dependent change in bone mineral density (BMD) after application of a porous polyimide film supporting bone marrow cells by single or twice seeding and culturing, to a bone injury site in a rat cranial bone loss model.

After harvesting femora and tibia of 8-week-old GFP transgenic rats and cutting off both ends of each bone, bone marrow cell masses were harvested by flushing with 10% FBS-added DMEM medium. The cell masses were pulverized by pipetting, and $1.0 \times 10^6$ bone marrow cells were seeded on the mesh surface (A-surface) of a 1.5 cm-square porous polyimide film and stationary cultured for 5 days in DMEM medium containing 10% FBS. After exchanging the DMEM medium, culturing was continued for 1 day. Next, 1.0×10⁶ bone marrow cells were seeded on the mesh surface (A-surface) of a porous polyimide film and stationary cultured for 5 days in DMEM medium containing 10% FBS. On the 6th day, the cell-adhered porous polyimide film was rinsed with phosphate buffer and further cultured for 1 day, after only changing the medium to DMEM. After general anesthesia of 9-week-old nude rats with 2-3% isoflurane, they were subjected to infiltration anesthesia in the field of operation, with 1/10,000 epinephrine-containing lidocaine. A region wider than the incision site was shaved, and then an incision was made at the top of the head on a straight line up to the subperiosteum, for sufficient delineation of the operating field. After detaching the dermal periosteal flap and exposing the parietal bone, a trephine bur was used to form two 4 mm-diameter circular bone loss sections under poured sterile physiological saline. The loss section was covered by the porous polyimide film on which the cells had been adhered and then cultured, in a manner so as to place the mesh surface (A-surface) in the wound area. After 2 weeks, 4 weeks and 8 weeks, the condition of healing of the loss section was measured, and healing of the wound area was periodically confirmed. The results are shown in FIGS. 9 to 11.

The invention claimed is:

1. A method of inducing differentiation from bone marrow cells derived from a mammal to hematocytes, comprising:
   (1) applying a first cell group consisting of the bone marrow cells to a porous polyimide film and culturing it;
   (2) applying a second cell group consisting of the bone marrow cells to the porous polyimide film after the culturing in step (1), and culturing it; and
   (3) adding a differentiation-inducing accelerating substance to the porous polyimide film after the culturing in step (2), and culturing, to accelerate differentiation from the bone marrow cells to the hematocytes,
   wherein the porous polyimide film has a three-layer structure consisting of an A-surface layer having a plurality of pores, a B-surface layer having a plurality of pores, and a macro-void layer sandwiched between the two surface layers,
   a mean pore size in the A-surface layer is smaller than a mean pore size in the B-surface layer, and
   the macro-void layer has a partition bonded to the A-surface layer and the B-surface layer, and a plurality of macro-voids surrounded by the partition, the A-surface layer, and the B-surface layer.

2. The method according to claim 1, further including recovering the hematocytes.

3. The method according to claim 1, wherein the hematocytes are erythroid progenitor cells or erythrocytes.

4. The method according to claim 1, wherein the porous polyimide film is a porous polyimide film including a polyimide obtained from a tetracarboxylic dianhydride and a diamine.

5. The method according to claim 4, wherein the porous polyimide film is a colored porous polyimide film obtained by forming a polyamic acid solution composition including a polyamic acid solution obtained from a tetracarboxylic dianhydride and a diamine, and a coloring precursor, and then heat treating it at 250° C. or higher.

6. The method according to claim 1, using two or more porous polyimide films layered either above and below or left and right in the cell culture medium.

7. The method according to claim 1, wherein the porous polyimide film is:
   i) folded,
   ii) wound into a roll,
   iii) connected as sheets or fragments by a filamentous structure, or
   iv) bound into a rope,
   and used by suspension or anchoring in the cell culture medium in the cell culturing vessel.

8. The method according to claim 1, wherein the differentiation-inducing accelerating substance is selected from the group consisting of colony-stimulating factor, granulocyte colony stimulating factor, stem-cell factor, stem cell growth factor-α, erythropoietin, thrombopoietin and interleukin.

9. The method according to claim 1, wherein the differentiation-inducing accelerating substance is erythropoietin.

* * * * *